US009234021B2

(12) United States Patent
Cochran et al.

(10) Patent No.: US 9,234,021 B2
(45) Date of Patent: *Jan. 12, 2016

(54) POLYPEPTIDES TARGETING VASCULAR ENDOTHELIAL GROWTH FACTOR RECEPTOR-2 AND ALPHA V BETA 3 INTEGRIN

(71) Applicant: The Board of Trustees of the Leland Stanford Junior University, Palo Alto, CA (US)

(72) Inventors: Jennifer R. Cochran, Stanford, CA (US); Adam Silverman, Redwood City, CA (US); Douglas Jones, Newton, MA (US); Niv Papo, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/257,772

(22) Filed: Apr. 21, 2014

(65) Prior Publication Data
US 2014/0356286 A1 Dec. 4, 2014

Related U.S. Application Data

(63) Continuation of application No. 13/145,059, filed as application No. PCT/US2010/021332 on Jan. 18, 2010, now Pat. No. 8,741,839.

(60) Provisional application No. 61/145,579, filed on Jan. 18, 2009.

(51) Int. Cl.
| | | |
|---|---|---|
| *A61K 38/04* | (2006.01) | |
| *C07K 2/00* | (2006.01) | |
| *A61K 38/00* | (2006.01) | |
| *C07K 14/515* | (2006.01) | |
| *A61K 38/18* | (2006.01) | |
| *A61K 47/48* | (2006.01) | |
| *C07K 14/475* | (2006.01) | |

(52) U.S. Cl.
CPC .............. *C07K 14/515* (2013.01); *A61K 38/18* (2013.01); *A61K 38/1858* (2013.01); *A61K 47/48007* (2013.01); *C07K 14/475* (2013.01); *A61K 38/1866* (2013.01); *A61K 2123/00* (2013.01)

(58) Field of Classification Search
None
See application file for complete search history.

(56) References Cited

U.S. PATENT DOCUMENTS

| | | | |
|---|---|---|---|
| 6,057,428 A | 5/2000 | Keyt et al. | |
| 6,541,008 B1 | 4/2003 | Wise et al. | |
| 7,090,834 B1 | 8/2006 | Cunningham et al. | |
| 2003/0027751 A1 | 2/2003 | Kovesdi et al. | |
| 2004/0014948 A1 | 1/2004 | Halkier et al. | |
| 2004/0038341 A1 | 2/2004 | Shibuya | |
| 2004/0052785 A1 | 3/2004 | Goodman et al. | |
| 2007/0025957 A1 | 2/2007 | Rosenblum et al. | |
| 2008/0031815 A1 | 2/2008 | Chen et al. | |
| 2013/0115210 A1 | 5/2013 | Kerber et al. | |

FOREIGN PATENT DOCUMENTS

| | | |
|---|---|---|
| WO | 02/081520 | 10/2002 |
| WO | 02/083851 A2 | 10/2002 |

OTHER PUBLICATIONS

Koivunen E, Wang B, Ruoslahti E. Phage libraries displaying cyclic peptides with different ring sizes: ligand specificities of the RGD-directed integrins. Biotechnology (N Y) 1995;13(3):265-70.*
Kuntz. Structure-based strategies for drug design and discovery. Science. 1992 257(5073):1078-1082.*
Miller et al Ligand binding to proteins: the binding landscape model. Protein Sci. Oct. 1997;6(10):2166-79.*
Carmeliet; et al., "Impaired myocardial angiogenesis and ischemic cardiomyopathy in mice lacking the vascular endothelial growth factor isoforms VEGF164 and VEGF188" Nature Medicine (May 1999), 5(5):495-502.
Cochran; et al., "Domain-level antibody epitope mapping through yeast surface display of epidermal growth factor receptor fragments" Journal of Immunological Methods (Apr. 2004 ), 287:(1-2):147-58.
Cochran; et al., "Improved mutants from directed evolution are biased to orthologous substitutions" Protein Engineering, Design & Selection (Jun. 2006), 19(6):245-253.
Hufton; et al., "Development and application of cytotoxic T lymphocyte-associated antigen 4 as a protein scaffold for the generation of novel binding ligands" FEBS Letters (Jun. 2000), 475(3):255-231.
Kim; et al., "Directed Evolution of the Epidermal Growth Factor Receptor Extracellular Domain for Expression in Yeast" Proteins (Mar. 2006), 62(4):1026-1035.
Papo; et al. "Antagonistic VEGF variants engineered to simultaneously bind to and inhibit VEGFR2 and alphavbeta3 integrin" PNAS (Aug. 2011), 108(34):14067-72.
Silverman; et al., "Engineered cystine-knot peptides that bind alpha(v)beta(3) integrin with antibody-like affinities" Journal of Molecular Biology (Jan. 2009), 385(4):1064-75.
Strieth; et al., "Antiangiogenic combination tumor therapy blocking alpha(v)-integrins and VEGF-receptor-2 increases therapeutic effects in vivo" International Journal of Cancer (Jul. 2006), 119(2):423-31.
Boesen; et al., "Single-chain vascular endothelial growth factor variant with antagonist activity", The Journal of Biological Chemistry (Oct. 2002), 277(43):40335-41.
Kiba; et al., "A set of loop-1 and -3 structures in the novel vascular endothelial growth factor (VEGF) family member, VEGF-ENZ-7, is essential for the activation of VEGFR-2 signaling", The Journal of Biological Chemistry (Apr. 2003), 278(15):13453-61.

(Continued)

*Primary Examiner* — Maher Haddad
(74) *Attorney, Agent, or Firm* — Bozicevic, Field & Francis LLP; Pamela Sherwood

(57) ABSTRACT

Polypeptides comprising variant vascular endothelial growth factor sequences are provided. The polypeptides are useful in cancer imaging, cancer diagnosis, monitoring and treatment as well as treatment of diseases characterized by excessive neovascularization.

2 Claims, 12 Drawing Sheets

(56) References Cited

OTHER PUBLICATIONS

Schlaeppi; et al., "Characterization of a new potent, in vivo neutralizing monoclonal antibody to human vascular endothelial growth factor", J Cancer Res Clin Oncol (1999), 125(6):336-42.

Skolnick; et al., "From genes to protein structure and function: novel applications of computational approaches in the genomic era", Trends in Biotechnology (Jan. 2000), 18(1):34-9.

Tosatto; et al., "Large-scale prediction of protein structure and function from sequence", Current Pharmaceutical Design (2006), 12(17):2067-86.

* cited by examiner

SEQUENCE LISTING

```
<160> NUMBER OF SEQ ID NOS: 70

<210> SEQ ID NO 1
<211> LENGTH: 121
<212> TYPE: PRT
<213> ORGANISM: H. sapiens

<400> SEQUENCE: 1

Ala Pro Met Ala Glu Gly Gly Gly Gln Asn His His Glu Val Val Lys
 1               5                  10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
               100                 105                 110

Gln Glu Lys Cys Asp Lys Pro Arg Arg
           115                 120

<210> SEQ ID NO 2
<211> LENGTH: 97
<212> TYPE: PRT
<213> ORGANISM: H. sapiens

<400> SEQUENCE: 2

Glu Val Val Lys Phe Met Asp Val Tyr Gln Arg Ser Tyr Cys His Pro
 1               5                  10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Glu Gly Leu Glu Cys Val Pro Thr Glu Glu Ser Asn Ile
    50                  55                  60

Thr Met Gln Ile Met Arg Ile Lys Pro His Gln Gly Gln His Ile Gly
65                  70                  75                  80

Glu Met Ser Phe Leu Gln His Asn Lys Cys Glu Cys Arg Pro Lys Lys
```

-continued

```
                85                  90                  95

Asp

<210> SEQ ID NO 3
<211> LENGTH: 212
<212> TYPE: PRT
<213> ORGANISM: H. sapiens

<400> SEQUENCE: 3

Tyr Val Glu Val Val Lys Phe Met Asp Val Tyr Gln Arg Ser Tyr Cys
  1               5                  10                  15

His Pro Ile Glu Thr Leu Val Asp Ile Phe Gln Glu Tyr Pro Asp Glu
                 20                  25                  30

Ile Glu Tyr Ile Phe Lys Pro Ser Cys Val Pro Leu Met Arg Cys Gly
             35                  40                  45

Gly Cys Cys Asn Asp Glu Gly Leu Glu Cys Val Pro Thr Glu Glu Ser
         50                  55                  60

Asn Ile Thr Met Gln Ile Met Arg Ile Lys Pro His Gln Gly Gln His
 65                  70                  75                  80

Ile Gly Glu Met Ser Phe Leu Gln His Asn Lys Cys Glu Cys Arg Pro
                 85                  90                  95

Lys Lys Asp Gly Ser Thr Ser Gly Ser Gly Lys Ser Ser Glu Gly Lys
                100                 105                 110

Gly Glu Val Val Lys Phe Met Asp Val Tyr Gln Arg Ser Tyr Cys His
                115                 120                 125

Pro Ile Glu Thr Leu Val Asp Ile Phe Gln Glu Tyr Pro Asp Glu Ile
            130                 135                 140

Glu Tyr Ile Phe Lys Pro Ser Cys Val Pro Leu Met Arg Cys Gly Gly
145                 150                 155                 160

Cys Cys Asn Asp Glu Gly Leu Glu Cys Val Pro Thr Glu Glu Ser Asn
                165                 170                 175

Ile Thr Met Gln Ile Met Arg Ile Lys Pro His Gln Gly Gln His Ile
                180                 185                 190

Gly Glu Met Ser Phe Leu Gln His Asn Lys Cys Glu Cys Arg Pro Lys
            195                 200                 205

Lys Asp Thr Arg
        210

<210> SEQ ID NO 4
<211> LENGTH: 212
<212> TYPE: PRT
<213> ORGANISM: H. sapiens

<400> SEQUENCE: 4

Tyr Val Glu Val Val Lys Ala Met Asp Val Tyr Gln Arg Ser Tyr Cys
  1               5                  10                  15

His Pro Ile Glu Thr Leu Val Asp Ile Phe Gln Glu Tyr Pro Asp Glu
                 20                  25                  30

Ile Glu Tyr Ile Phe Lys Pro Ser Cys Val Pro Leu Met Arg Cys Gly
             35                  40                  45

Gly Cys Cys Asn Asp Ala Gly Leu Glu Cys Val Pro Thr Glu Glu Ser
         50                  55                  60

Asn Ile Thr Met Gln Ile Met Arg Ile Lys Pro His Gln Gly Gln His
 65                  70                  75                  80

Ile Gly Glu Met Ser Phe Leu Gln His Asn Lys Cys Glu Cys Arg Pro
                 85                  90                  95
```

```
Lys Lys Asp Gly Ser Thr Ser Gly Ser Gly Lys Ser Ser Glu Gly Lys
                100                 105                 110

Gly Glu Val Val Lys Phe Met Asp Val Tyr Gln Arg Ser Tyr Cys His
            115                 120                 125

Pro Ile Glu Thr Leu Val Asp Ile Phe Gln Glu Tyr Pro Asp Glu Ile
        130                 135                 140

Glu Tyr Ala Phe Lys Pro Ser Cys Val Pro Leu Met Arg Cys Gly Gly
145                 150                 155                 160

Cys Cys Asn Asp Glu Gly Leu Glu Cys Val Pro Thr Glu Glu Ser Asn
                165                 170                 175

Ile Thr Met Gln Ile Met Arg Ala Lys Pro His Gln Gly Gln His Ile
            180                 185                 190

Gly Glu Met Ser Phe Leu Gln His Asn Lys Cys Glu Cys Arg Pro Lys
        195                 200                 205

Lys Asp Thr Arg
        210

<210> SEQ ID NO 5
<211> LENGTH: 212
<212> TYPE: PRT
<213> ORGANISM: H. sapiens

<400> SEQUENCE: 5

Glu Val Val Lys Ala Met Asp Val Tyr Gln Arg Ser Tyr Cys His Pro
  1               5                  10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
 50                  55                  60

Thr Met Gln Ile Met Arg Ile Lys Pro His Gln Gly Gln His Ile Gly
 65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu Tyr
    130                 135                 140

Ala Phe Lys Pro Ser Cys Val Pro Leu Met Arg Cys Gly Gly Cys Cys
145                 150                 155                 160

Asn Asp Glu Gly Leu Glu Cys Val Pro Thr Glu Glu Ser Asn Ile Thr
                165                 170                 175

Met Gln Ile Met Arg Pro His Arg Gly Asp Ala Gly Val His Ile
            180                 185                 190

Gly Glu Met Ser Phe Leu Gln His Asn Lys Cys Glu Cys Arg Pro Lys
        195                 200                 205

Lys Asp Thr Arg
        210

<210> SEQ ID NO 6
<211> LENGTH: 212
<212> TYPE: PRT
```

<213> ORGANISM: H. sapiens

<400> SEQUENCE: 6

Glu Val Val Lys Ala Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro His Gln Gly Gln His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu Tyr
    130                 135                 140

Ala Phe Lys Pro Ser Cys Val Pro Leu Met Arg Cys Gly Gly Cys Cys
145                 150                 155                 160

Asn Asp Glu Gly Leu Glu Cys Val Pro Thr Glu Glu Ser Asn Ile Thr
                165                 170                 175

Met Gln Ile Met Arg Pro Gly Gly Arg Gly Asp Ser Ala Tyr His Ile
            180                 185                 190

Gly Glu Met Ser Phe Leu Gln His Asn Lys Cys Glu Cys Arg Pro Lys
        195                 200                 205

Lys Asp Thr Arg
    210

<210> SEQ ID NO 7
<211> LENGTH: 214
<212> TYPE: PRT
<213> ORGANISM: H. sapiens

<400> SEQUENCE: 7

Glu Val Val Lys Ala Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro His Gln Gly Gln His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu Tyr

```
            130                 135                 140
Ala Phe Lys Pro Ser Cys Val Pro Leu Met Arg Cys Gly Gly Cys Cys
145                 150                 155                 160

Asn Asp Glu Gly Leu Glu Cys Val Pro Thr Glu Ser Asn Ile Thr
                165                 170                 175

Met Gln Ile Met Arg Pro Ser Val Arg Arg Gly Asp Ser Pro Ala Ser
                180                 185                 190

His Ile Gly Glu Met Ser Phe Leu Gln His Asn Lys Cys Glu Cys Arg
                195                 200                 205

Pro Lys Lys Asp Thr Arg
    210

<210> SEQ ID NO 8
<211> LENGTH: 212
<212> TYPE: PRT
<213> ORGANISM: H. sapiens

<400> SEQUENCE: 8

Glu Val Val Lys Ala Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
            35                  40                  45

Cys Asn Asp Ala Gly Leu Glu Cys Val Pro Thr Glu Glu Ser Asn Ile
50                  55                  60

Thr Met Gln Ile Met Arg Ile Lys Pro His Gln Gly Gln His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
                100                 105                 110

Val Val Lys Phe Met Asp Val Tyr Gln Arg Ser Tyr Cys His Pro Ile
                115                 120                 125

Glu Thr Leu Val Asp Ile Phe Gln Glu Tyr Pro Asp Glu Ile Glu Tyr
            130                 135                 140

Ala Phe Lys Pro Ser Cys Val Pro Leu Met Arg Cys Gly Gly Cys Cys
145                 150                 155                 160

Asn Asp Glu Gly Leu Glu Cys Val Pro Thr Glu Glu Ser Asn Ile Thr
                165                 170                 175

Met Gln Ile Met Arg Pro Ala Ser Arg Gly Asp Ser Pro His Ile
                180                 185                 190

Gly Glu Met Ser Phe Leu Gln His Asn Lys Cys Glu Cys Arg Pro Lys
                195                 200                 205

Lys Asp Thr Arg
    210

<210> SEQ ID NO 9
<211> LENGTH: 208
<212> TYPE: PRT
<213> ORGANISM: H. sapiens

<400> SEQUENCE: 9

Glu Val Val Lys Ala Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
```

```
                     20                  25                  30
Tyr Ile Phe Lys Pro Ser Cys Val Pro Leu Met Arg Cys Gly Gly Cys
                 35                  40                  45

Cys Asn Asp Ala Gly Leu Glu Cys Val Pro Thr Glu Glu Ser Asn Ile
 50                  55                  60

Thr Met Gln Ile Met Arg Ile Lys Pro His Gln Gly Gln His Ile Gly
 65                  70                  75                  80

Glu Met Ser Phe Leu Gln His Asn Lys Cys Glu Cys Arg Pro Lys Lys
                 85                  90                  95

Asp Gly Ser Thr Ser Gly Ser Gly Lys Ser Ser Glu Gly Lys Gly Glu
                100                 105                 110

Val Val Lys Phe Met Asp Val Tyr Gln Arg Ser Tyr Cys His Pro Ile
                115                 120                 125

Glu Thr Leu Val Asp Ile Phe Gln Glu Tyr Pro Asp Glu Ile Glu Tyr
                130                 135                 140

Ala Phe Lys Pro Ser Cys Val Pro Leu Met Arg Cys Gly Gly Cys Cys
145                 150                 155                 160

Asn Asp Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
                180                 185                 190

Met Ser Phe Leu Gln His Asn Lys Cys Glu Cys Arg Pro Lys Lys Asp
                195                 200                 205

<210> SEQ ID NO 10
<211> LENGTH: 208
<212> TYPE: PRT
<213> ORGANISM: H. sapiens

<400> SEQUENCE: 10

Glu Val Val Lys Ala Met Asp Val Tyr Gln Arg Ser Tyr Cys His Pro
  1               5                  10                  15

Ile Glu Thr Leu Val Asp Ile Phe Gln Glu Tyr Pro Asp Glu Ile Glu
                 20                  25                  30

Tyr Ile Phe Lys Pro Ser Cys Val Pro Leu Met Arg Cys Gly Gly Cys
                 35                  40                  45

Cys Asn Asp Ala Gly Leu Glu Cys Val Pro Thr Glu Glu Ser Asn Ile
 50                  55                  60

Thr Met Gln Ile Met Arg Ile Lys Pro Tyr Gln Gly His His Ile Gly
 65                  70                  75                  80

Glu Met Ser Phe Leu Gln His Asn Lys Cys Glu Cys Arg Pro Lys Lys
                 85                  90                  95

Asp Gly Ser Thr Pro Gly Ser Gly Lys Ser Ser Glu Gly Lys Gly Glu
                100                 105                 110

Val Val Lys Leu Met Asp Val Tyr Gln Arg Ser Tyr Cys His Pro Ile
                115                 120                 125

Glu Thr Leu Val Asp Ile Phe Gln Glu Tyr Pro Asp Glu Ile Glu Tyr
                130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Val Gly Glu
                180                 185                 190
```

```
Met Ser Phe Leu Gln His Asn Glu Cys Glu Cys Arg Pro Lys Lys Asp
        195                 200                 205

<210> SEQ ID NO 11
<211> LENGTH: 208
<212> TYPE: PRT
<213> ORGANISM: H. sapiens

<400> SEQUENCE: 11

Glu Val Val Lys Ala Met Asp Val Tyr Gln Arg Ser Tyr Cys His Pro
 1               5                  10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro Tyr Arg Gly His His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu His
    130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
            180                 185                 190

Met Ser Phe Leu Gln His Asn Lys Cys Glu Cys Arg Pro Lys Lys Asp
        195                 200                 205

<210> SEQ ID NO 12
<211> LENGTH: 208
<212> TYPE: PRT
<213> ORGANISM: H. sapiens

<400> SEQUENCE: 12

Glu Ile Val Lys Ala Arg Asp Val Tyr Gln Arg Ser Tyr Cys His Pro
 1               5                  10                  15

Ile Glu Thr Leu Val Asp Ile Leu Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro Tyr Gln Gly His His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Lys Ser Ser Glu Gly Lys Gly Glu
            100                 105                 110
```

```
Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu Tyr
        130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Thr Gly Glu
                180                 185                 190

Met Ser Phe Leu Gln His Asn Lys Cys Glu Cys Arg Pro Lys Lys Asp
                195                 200                 205
```

<210> SEQ ID NO 13
<211> LENGTH: 208
<212> TYPE: PRT
<213> ORGANISM: H. sapiens

<400> SEQUENCE: 13

```
Glu Val Ala Lys Ala Met Asp Val Tyr Gln Lys Ser Tyr Cys His Pro
1               5                   10                  15

Ile Glu Thr Leu Val Asp Ile Leu Gln Glu Tyr Pro Asp Glu Ile Gly
                20                  25                  30

Tyr Ile Phe Lys Pro Ser Cys Val Pro Leu Met Arg Cys Gly Gly Cys
            35                  40                  45

Cys Asn Asp Ala Gly Leu Glu Cys Val Pro Thr Glu Glu Ser Asn Ile
        50                  55                  60

Thr Met Gln Ile Met Arg Ile Lys Pro Tyr Gln Gly Gln His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
                100                 105                 110

Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Lys Ile Glu Tyr
        130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Thr Arg Ala Lys Pro His Gln Gly Gln His Ile Gly Glu
                180                 185                 190

Met Ser Phe Leu Gln His Asn Lys Cys Glu Cys Arg Pro Lys Lys Asp
                195                 200                 205
```

<210> SEQ ID NO 14
<211> LENGTH: 208
<212> TYPE: PRT
<213> ORGANISM: H. sapiens

<400> SEQUENCE: 14

```
Glu Val Val Lys Ala Met Asp Val Tyr Gln Arg Ser Tyr Cys His Pro
1               5                   10                  15

Ile Glu Thr Leu Val Asp Ile Leu Gln Glu Tyr Pro Asp Glu Ile Gly
                20                  25                  30
```

```
Tyr Ile Phe Lys Pro Ser Cys Val Pro Leu Met Arg Cys Gly Gly Cys
            35                  40                  45

Cys Asn Gly Ala Gly Leu Glu Cys Val Pro Thr Glu Glu Ser Asn Ile
 50                  55                  60

Thr Met Gln Ile Met Arg Ile Lys Pro His Arg Gly Gln His Ile Gly
 65                  70                  75                  80

Glu Met Ser Phe Leu Gln His Asn Lys Cys Glu Cys Arg Pro Lys Lys
                 85                  90                  95

Asp Gly Ser Thr Ser Gly Ser Gly Lys Ser Ser Glu Gly Lys Gly Glu
                100                 105                 110

Val Val Arg Phe Met Asp Val Tyr Gln Arg Ser Tyr Cys His Pro Ile
                115                 120                 125

Glu Thr Leu Val Asp Ile Phe Gln Glu Tyr Pro Asn Glu Ile Glu Tyr
            130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
                180                 185                 190

Met Ser Phe Leu Gln His Asn Lys Cys Glu Cys Arg Pro Lys Lys Asp
            195                 200                 205

<210> SEQ ID NO 15
<211> LENGTH: 208
<212> TYPE: PRT
<213> ORGANISM: H. sapiens

<400> SEQUENCE: 15

Glu Ala Val Lys Ala Met Asp Val Tyr Gln Arg Ser Tyr Cys His Pro
  1               5                  10                  15

Ile Glu Thr Leu Val Asp Ile Phe Gln Glu Tyr Pro Asp Glu Ile Glu
             20                  25                  30

Tyr Ile Phe Lys Pro Ser Cys Val Pro Leu Met Arg Cys Gly Gly Cys
            35                  40                  45

Cys Asn Asp Ala Gly Leu Glu Cys Val Pro Thr Glu Glu Ser Asn Ile
 50                  55                  60

Thr Met Gln Ile Met Arg Ile Lys Pro His Arg Gly Gln His Ile Gly
 65                  70                  75                  80

Glu Met Ser Phe Leu Gln His Asn Lys Cys Glu Cys Arg Pro Lys Lys
                 85                  90                  95

Asp Gly Ser Thr Ser Gly Ser Gly Lys Ser Ser Gly Gly Lys Gly Glu
                100                 105                 110

Val Val Lys Phe Met Asp Val Tyr Gln Arg Ser Tyr Cys His Pro Ile
                115                 120                 125

Glu Thr Leu Val Asp Val Phe Gln Glu Tyr Pro Asp Glu Ile Glu Tyr
            130                 135                 140

Ala Ser Glu Pro Ser Cys Val Pro Leu Met Arg Cys Gly Gly Cys Cys
145                 150                 155                 160

Asn His Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
                180                 185                 190

Met Ser Phe Leu Gln His Asn Lys Cys Glu Cys Arg Pro Lys Lys Asp
            195                 200                 205
```

<210> SEQ ID NO 16
<211> LENGTH: 208
<212> TYPE: PRT
<213> ORGANISM: H. sapiens

<400> SEQUENCE: 16

Glu Val Val Lys Ala Met Gly Val Tyr Gln Arg Ser Tyr Cys His Pro
1               5                   10                  15

Ile Glu Thr Leu Val Asp Ile Ser Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro His Gln Gly His Arg Ile Gly
65                  70                  75                  80

Glu Met Ser Phe Leu Gln His Asp Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Arg Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu Tyr
    130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Val Arg Ala Lys Pro His Gln Gly Gln His Ile Gly Glu
            180                 185                 190

Met Ser Phe Leu Gln His Asn Lys Cys Glu Cys Arg Pro Lys Lys Asp
        195                 200                 205

<210> SEQ ID NO 17
<211> LENGTH: 208
<212> TYPE: PRT
<213> ORGANISM: H. sapiens

<400> SEQUENCE: 17

Glu Val Val Lys Ala Met Asp Val Tyr Arg Arg Ser Tyr Cys His Pro
1               5                   10                  15

Val Glu Thr Ser Val Asp Ile Leu Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Thr
    50                  55                  60

Thr Met Gln Ile Met Arg Ile Lys Pro Tyr Arg Gly Gln His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Lys Phe Met Asp Val Tyr Gln Arg Ser Tyr Cys His Pro Ile
        115                 120                 125

```
Glu Thr Leu Val Asp Ile Phe Gln Glu Tyr Pro Asp Glu Ile Glu Tyr
    130                 135                 140

Ala Phe Lys Pro Ser Cys Val Ser Leu Met Arg Cys Gly Gly Cys
145                 150                 155                 160

Asn Asn Glu Gly Leu Glu Cys Val Pro Thr Glu Glu Ser Asn Ile Thr
                165                 170                 175

Val Gln Ile Met Gly Ala Lys Pro His Gln Gly Gln His Ile Gly Glu
            180                 185                 190

Met Ser Phe Leu Gln His Asn Lys Cys Glu Cys Arg Pro Lys Lys Asp
            195                 200                 205

<210> SEQ ID NO 18
<211> LENGTH: 208
<212> TYPE: PRT
<213> ORGANISM: H. sapiens

<400> SEQUENCE: 18

Glu Val Ala Lys Ala Met Asp Val Tyr Gln Arg Ser Tyr Cys His Pro
1               5                   10                  15

Ile Glu Thr Leu Val Asp Ile Leu Gln Glu Tyr Pro Asp Glu Ile Gly
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro His Gln Gly His Arg Ile Gly
65                  70                  75                  80

Glu Met Ser Phe Leu Gln His Asp Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu Tyr
    130                 135                 140

Ala Phe Lys Leu Pro Cys Val Pro Leu Met Arg Cys Ser Gly Tyr Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
            180                 185                 190

Met Ser Phe Leu Gln His Asn Lys Cys Glu Cys Arg Pro Lys Lys Asp
            195                 200                 205

<210> SEQ ID NO 19
<211> LENGTH: 208
<212> TYPE: PRT
<213> ORGANISM: H. sapiens

<400> SEQUENCE: 19

Glu Val Val Lys Ala Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45
```

```
Cys Asn Asp Ala Gly Leu Glu Cys Val Pro Thr Glu Glu Ser Asn Ile
         50                  55                  60

Thr Met Gln Ile Met Arg Ile Lys Pro His Gln Gly Gln His Ile Gly
 65                  70                  75                  80

Glu Met Ser Phe Leu Gln His Asn Lys Cys Glu Cys Arg Pro Lys Lys
                 85                  90                  95

Asp Gly Ser Thr Ser Gly Ser Gly Lys Ser Ser Glu Gly Lys Gly Glu
                100                 105                 110

Val Val Lys Phe Met Asp Val Tyr Gln Arg Ser Tyr Cys His Pro Ile
                115                 120                 125

Glu Thr Leu Val Asp Ile Phe Gln Glu Tyr Pro Asp Glu Ile Glu Tyr
        130                 135                 140

Ala Phe Lys Pro Ser Cys Val Pro Leu Met Arg Cys Gly Gly Cys Cys
145                 150                 155                 160

Asn Asp Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
                180                 185                 190

Met Ser Phe Leu Gln His Asn Lys Cys Glu Cys Arg Pro Lys Lys Asp
                195                 200                 205
```

<210> SEQ ID NO 20
<211> LENGTH: 208
<212> TYPE: PRT
<213> ORGANISM: H. sapiens

<400> SEQUENCE: 20

```
Glu Val Val Lys Ala Met Asp Val Tyr Gln Arg Ser Tyr Cys His Pro
  1               5                  10                  15

Ile Glu Thr Leu Val Asp Ile Phe Gln Glu Tyr Pro Asp Glu Ile Glu
                 20                  25                  30

Tyr Ile Phe Lys Pro Ser Cys Val Pro Leu Met Arg Cys Gly Gly Cys
                 35                  40                  45

Cys Asn Asp Ala Gly Leu Glu Cys Val Pro Thr Glu Glu Ser Asn Ile
         50                  55                  60

Thr Met Gln Ile Met Arg Ile Lys Pro Tyr Gln Gly His His Ile Gly
 65                  70                  75                  80

Glu Met Ser Phe Leu Gln His Asn Lys Cys Glu Cys Arg Pro Lys Lys
                 85                  90                  95

Asp Gly Ser Thr Pro Gly Ser Gly Lys Ser Ser Glu Gly Lys Gly Glu
                100                 105                 110

Val Val Lys Leu Met Asp Val Tyr Gln Arg Ser Tyr Cys His Pro Ile
                115                 120                 125

Glu Thr Leu Val Asp Ile Phe Gln Glu Tyr Pro Asp Glu Ile Glu Tyr
        130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Val Gly Glu
                180                 185                 190

Met Ser Phe Leu Gln His Asn Glu Cys Glu Cys Arg Pro Lys Lys Asp
                195                 200                 205
```

```
<210> SEQ ID NO 21
<211> LENGTH: 208
<212> TYPE: PRT
<213> ORGANISM: H. sapiens

<400> SEQUENCE: 21
```

| | | | | | | | | | | | | | | | |
|---|---|---|---|---|---|---|---|---|---|---|---|---|---|---|---|
| Glu | Val | Val | Lys | Ala | Met | Asp | Val | Tyr | Gln | Arg | Ser | Tyr | Cys | His | Pro |
| 1 | | | | 5 | | | | | 10 | | | | | 15 | |
| Ile | Glu | Thr | Leu | Val | Asp | Ile | Phe | Gln | Glu | Tyr | Pro | Asp | Glu | Ile | Glu |
| | | | 20 | | | | | 25 | | | | | 30 | | |
| Tyr | Ile | Phe | Lys | Pro | Ser | Cys | Val | Pro | Leu | Met | Arg | Cys | Gly | Gly | Cys |
| | | | | 35 | | | | | 40 | | | | | 45 | |
| Cys | Asn | Asp | Ala | Gly | Leu | Glu | Cys | Val | Pro | Thr | Glu | Glu | Ser | Asn | Ile |
| | 50 | | | | | 55 | | | | | 60 | | | | |
| Thr | Met | Gln | Ile | Met | Arg | Ile | Lys | Pro | Tyr | Arg | Gly | His | His | Ile | Gly |
| 65 | | | | | 70 | | | | | 75 | | | | | 80 |
| Glu | Met | Ser | Phe | Leu | Gln | His | Asn | Lys | Cys | Glu | Cys | Arg | Pro | Lys | Lys |
| | | | | 85 | | | | | 90 | | | | | 95 | |
| Asp | Gly | Ser | Thr | Ser | Gly | Ser | Gly | Lys | Ser | Ser | Glu | Gly | Lys | Gly | Glu |
| | | | 100 | | | | | 105 | | | | | 110 | | |
| Val | Val | Lys | Phe | Met | Asp | Val | Tyr | Gln | Arg | Ser | Tyr | Cys | His | Pro | Ile |
| | | | | 115 | | | | | 120 | | | | | 125 | |
| Glu | Thr | Leu | Val | Asp | Ile | Phe | Gln | Glu | Tyr | Pro | Asp | Glu | Ile | Glu | His |
| | 130 | | | | | 135 | | | | | 140 | | | | |
| Ala | Phe | Lys | Pro | Ser | Cys | Val | Pro | Leu | Met | Arg | Cys | Gly | Gly | Cys | Cys |
| 145 | | | | | 150 | | | | | 155 | | | | | 160 |
| Asn | Asn | Glu | Gly | Leu | Glu | Cys | Val | Pro | Thr | Glu | Glu | Ser | Asn | Ile | Thr |
| | | | | 165 | | | | | 170 | | | | | 175 | |
| Met | Gln | Ile | Met | Arg | Ala | Lys | Pro | His | Gln | Gly | Gln | His | Ile | Gly | Glu |
| | | | 180 | | | | | 185 | | | | | 190 | | |
| Met | Ser | Phe | Leu | Gln | His | Asn | Lys | Cys | Glu | Cys | Arg | Pro | Lys | Lys | Asp |
| | | | | 195 | | | | | 200 | | | | | 205 | |

```
<210> SEQ ID NO 22
<211> LENGTH: 208
<212> TYPE: PRT
<213> ORGANISM: H. sapiens

<400> SEQUENCE: 22
```

| | | | | | | | | | | | | | | | |
|---|---|---|---|---|---|---|---|---|---|---|---|---|---|---|---|
| Glu | Ile | Val | Lys | Ala | Arg | Asp | Val | Tyr | Gln | Arg | Ser | Tyr | Cys | His | Pro |
| 1 | | | | 5 | | | | | 10 | | | | | 15 | |
| Ile | Glu | Thr | Leu | Val | Asp | Ile | Leu | Gln | Glu | Tyr | Pro | Asp | Glu | Ile | Glu |
| | | | 20 | | | | | 25 | | | | | 30 | | |
| Tyr | Ile | Phe | Lys | Pro | Ser | Cys | Val | Pro | Leu | Met | Arg | Cys | Gly | Gly | Cys |
| | | | | 35 | | | | | 40 | | | | | 45 | |
| Cys | Asn | Asp | Ala | Gly | Leu | Glu | Cys | Val | Pro | Thr | Glu | Glu | Ser | Asn | Ile |
| | 50 | | | | | 55 | | | | | 60 | | | | |
| Thr | Met | Gln | Ile | Met | Arg | Ile | Lys | Pro | Tyr | Gln | Gly | His | His | Ile | Gly |
| 65 | | | | | 70 | | | | | 75 | | | | | 80 |
| Glu | Met | Ser | Phe | Leu | Gln | His | Asn | Lys | Cys | Glu | Cys | Arg | Pro | Lys | Lys |
| | | | | 85 | | | | | 90 | | | | | 95 | |
| Asp | Gly | Ser | Thr | Ser | Gly | Ser | Ser | Lys | Ser | Glu | Gly | Lys | Gly | Glu | |
| | | | 100 | | | | | 105 | | | | | 110 | | |
| Val | Val | Lys | Phe | Met | Asp | Val | Tyr | Gln | Arg | Ser | Tyr | Cys | His | Pro | Ile |
| | | | | 115 | | | | | 120 | | | | | 125 | |
| Glu | Thr | Leu | Val | Asp | Ile | Phe | Gln | Glu | Tyr | Pro | Asp | Glu | Ile | Glu | Tyr |

```
            130                 135                 140
Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Thr Gly Glu
            180                 185                 190

Met Ser Phe Leu Gln His Asn Lys Cys Glu Cys Arg Pro Lys Lys Asp
        195                 200                 205
```

<210> SEQ ID NO 23
<211> LENGTH: 208
<212> TYPE: PRT
<213> ORGANISM: H. sapiens

<400> SEQUENCE: 23

```
Glu Val Ala Lys Ala Met Asp Val Tyr Gln Lys Ser Tyr Cys His Pro
1               5                   10                  15

Ile Glu Thr Leu Val Asp Ile Leu Gln Glu Tyr Pro Asp Glu Ile Gly
                20                  25                  30

Tyr Ile Phe Lys Pro Ser Cys Val Pro Leu Met Arg Cys Gly Gly Cys
            35                  40                  45

Cys Asn Asp Ala Gly Leu Glu Cys Val Pro Thr Glu Glu Ser Asn Ile
50                  55                  60

Thr Met Gln Ile Met Arg Ile Lys Pro Tyr Gln Gly Gln His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Lys Ile Glu Tyr
    130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Thr Arg Ala Lys Pro His Gln Gly Gln His Ile Gly Glu
            180                 185                 190

Met Ser Phe Leu Gln His Asn Lys Cys Glu Cys Arg Pro Lys Lys Asp
        195                 200                 205
```

<210> SEQ ID NO 24
<211> LENGTH: 208
<212> TYPE: PRT
<213> ORGANISM: H. sapiens

<400> SEQUENCE: 24

```
Glu Val Val Lys Ala Met Asp Val Tyr Gln Arg Ser Tyr Cys His Pro
1               5                   10                  15

Ile Glu Thr Leu Val Asp Ile Leu Gln Glu Tyr Pro Asp Glu Ile Gly
                20                  25                  30

Tyr Ile Phe Lys Pro Ser Cys Val Pro Leu Met Arg Cys Gly Gly Cys
            35                  40                  45

Cys Asn Gly Ala Gly Leu Glu Cys Val Pro Thr Glu Glu Ser Asn Ile
```

Thr Met Gln Ile Met Arg Ile Lys Pro His Arg Gly Gln His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Arg Phe Met Asp Val Tyr Gln Arg Ser Tyr Cys His Pro Ile
            115                 120                 125

Glu Thr Leu Val Asp Ile Phe Gln Glu Tyr Pro Asn Glu Ile Glu Tyr
            130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
            180                 185                 190

Met Ser Phe Leu Gln His Asn Lys Cys Glu Cys Arg Pro Lys Lys Asp
            195                 200                 205

<210> SEQ ID NO 25
<211> LENGTH: 208
<212> TYPE: PRT
<213> ORGANISM: H. sapiens

<400> SEQUENCE: 25

Glu Ala Val Lys Ala Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
                20                  25                  30

Tyr Ile Phe Lys Pro Ser Cys Val Pro Leu Met Arg Cys Gly Gly Cys
            35                  40                  45

Cys Asn Asp Ala Gly Leu Glu Cys Val Pro Thr Glu Glu Ser Asn Ile
50                  55                  60

Thr Met Gln Ile Met Arg Ile Lys Pro His Arg Gly Gln His Ile Gly
65                  70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Gly Gly Lys Gly Glu
            100                 105                 110

Val Val Lys Phe Met Asp Val Tyr Gln Arg Ser Tyr Cys His Pro Ile
            115                 120                 125

Glu Thr Leu Val Asp Val Phe Gln Glu Tyr Pro Asp Glu Ile Glu Tyr
            130                 135                 140

Ala Ser Glu Pro Ser Cys Val Pro Leu Met Arg Cys Gly Gly Cys Cys
145                 150                 155                 160

Asn His Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
            180                 185                 190

Met Ser Phe Leu Gln His Asn Lys Cys Glu Cys Arg Pro Lys Lys Asp
            195                 200                 205

<210> SEQ ID NO 26
<211> LENGTH: 208

<212> TYPE: PRT
<213> ORGANISM: H. sapiens

<400> SEQUENCE: 26

Glu Val Val Lys Ala Met Gly Val Tyr Gln Arg Ser Tyr Cys His Pro
1               5                   10                  15

Ile Glu Thr Leu Val Asp Ile Ser Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro His Gln Gly His Arg Ile Gly
65              70                  75                  80

Glu Met Ser Phe Leu Gln His Asp Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Arg Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu Tyr
    130                 135                 140

Ala Phe Lys Pro Ser Cys Val Pro Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Met Gln Ile Val Arg Ala Lys Pro His Gln Gly Gln His Ile Gly Glu
            180                 185                 190

Met Ser Phe Leu Gln His Asn Lys Cys Glu Cys Arg Pro Lys Lys Asp
        195                 200                 205

<210> SEQ ID NO 27
<211> LENGTH: 208
<212> TYPE: PRT
<213> ORGANISM: H. sapiens

<400> SEQUENCE: 27

Glu Val Val Lys Ala Met Asp Val Tyr Arg Arg Ser Tyr Cys His Pro
1               5                   10                  15

Val Glu Thr Ser Val Asp Ile Leu Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Thr
    50                  55                  60

Thr Met Gln Ile Met Arg Ile Lys Pro Tyr Arg Gly Gln His Ile Gly
65              70                  75                  80

Glu Met Ser Phe Leu Gln His Asn Lys Cys Glu Cys Arg Pro Lys Lys
                85                  90                  95

Asp Gly Ser Thr Ser Gly Ser Gly Lys Ser Ser Glu Gly Lys Gly Glu
            100                 105                 110

Val Val Lys Phe Met Asp Val Tyr Gln Arg Ser Tyr Cys His Pro Ile
        115                 120                 125

Glu Thr Leu Val Asp Ile Phe Gln Glu Tyr Pro Asp Glu Ile Glu Tyr
    130                 135                 140

```
Ala Phe Lys Pro Ser Cys Val Ser Leu Met Arg Cys Gly Gly Cys Cys
145                 150                 155                 160

Asn Asn Glu Gly Leu Glu Cys Val Pro Thr Glu Glu Ser Asn Ile Thr
                165                 170                 175

Val Gln Ile Met Gly Ala Lys Pro His Gln Gly Gln His Ile Gly Glu
                180                 185                 190

Met Ser Phe Leu Gln His Asn Lys Cys Glu Cys Arg Pro Lys Lys Asp
                195                 200                 205
```

<210> SEQ ID NO 28
<211> LENGTH: 208
<212> TYPE: PRT
<213> ORGANISM: H. sapiens

<400> SEQUENCE: 28

```
Glu Val Ala Lys Ala Met Asp Val Tyr Gln Arg Ser Tyr Cys His Pro
1                   5                   10                  15

Ile Glu Thr Leu Val Asp Ile Leu Gln Glu Tyr Pro Asp Glu Ile Gly
                20                  25                  30

Tyr Ile Phe Lys Pro Ser Cys Val Pro Leu Met Arg Cys Gly Gly Cys
                35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro His Gln Gly Gln His Arg Ile Gly
65                  70                  75                  80

Glu Met Ser Phe Leu Gln His Asp Lys Cys Glu Cys Arg Pro Lys Lys
                85                  90                  95

Asp Gly Ser Thr Ser Gly Ser Gly Lys Ser Ser Glu Gly Lys Gly Glu
                100                 105                 110

Val Val Lys Phe Met Asp Val Tyr Gln Arg Ser Tyr Cys His Pro Ile
                115                 120                 125

Glu Thr Leu Val Asp Ile Phe Gln Glu Tyr Pro Asp Glu Ile Glu Tyr
                130                 135                 140

Ala Phe Lys Leu Pro Cys Val Pro Leu Met Arg Cys Ser Gly Tyr Cys
145                 150                 155                 160

Asn Asn Glu Gly Leu Glu Cys Val Pro Thr Glu Glu Ser Asn Ile Thr
                165                 170                 175

Met Gln Ile Met Arg Ala Lys Pro His Gln Gly Gln His Ile Gly Glu
                180                 185                 190

Met Ser Phe Leu Gln His Asn Lys Cys Glu Cys Arg Pro Lys Lys Asp
                195                 200                 205
```

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

```
Pro Phe Gly Thr Arg Gly Asp Ser Ser
1                   5
```

<210> SEQ ID NO 30
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 30

Ser Gly Glu Arg Gly Asp Gly Pro Thr
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide

<400> SEQUENCE: 31

Ser Asp Gly Arg Gly Asp Gly Ser Val
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide

<400> SEQUENCE: 32

Pro Ile Gly Arg Gly Asp Gly Ser Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic peptide

<400> SEQUENCE: 33

Leu Ala Glu Arg Gly Asp Ser Ser Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide

<400> SEQUENCE: 34

Pro Thr Gly Arg Gly Asp Leu Gly Ala
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide

<400> SEQUENCE: 35

Arg Gly Ile Arg Gly Asp Ser Gly Ala
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 36

Val Gly Gly Arg Gly Asp Val Gly Val
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

Ile Thr Ala Arg Gly Asp Ser Phe Gly
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Ile Thr Glu Arg Gly Asp Ser Gly His
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Pro Gln Ala Arg Gly Asp Arg Ser Asp
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Ser Arg Thr Arg Gly Asp Ala Ser Asp
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide

<400> SEQUENCE: 41

Pro Ala Ala Arg Gly Asp Gly Gly Leu
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42
```

```
Pro Val Ala Arg Gly Asp Ser Gly Ala
1               5
```

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

```
Pro Gln Gln Arg Gly Asp Gly Pro His
1               5
```

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

```
Pro Leu Pro Arg Gly Asp Gly Gln Arg
1               5
```

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

```
His Ala Gly Arg Gly Asp Ser Pro Ser
1               5
```

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

```
Thr Ser Leu Arg Gly Asp Thr Thr Trp
1               5
```

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

```
Pro Asn Phe Arg Gly Asp Glu Ala Tyr
1               5
```

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Ala Gly Val Pro Arg Gly Asp Ser Pro
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Pro Arg Ser Thr Arg Gly Asp Ser Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Pro Phe Gly Val Arg Gly Asp Asp Asn
1               5

<210> SEQ ID NO 51
<211> LENGTH: 11
<212> TYPE: PRT
<213> ORGANISM: Artificial Sequence
<220> FEATURE:
<223> OTHER INFORMATION: Synthetic peptide

<400> SEQUENCE: 51

Gly Phe Pro Phe Arg Gly Asp Ser Pro Ala Ser
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic peptide

<400> SEQUENCE: 52

Pro Ser Val Arg Arg Gly Asp Ser Pro Ala Ser
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Pro Phe Ala Val Arg Gly Asp Arg Pro
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Pro Trp Pro Arg Arg Gly Asp Leu Pro

```
<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

Pro Ser Gly Gly Arg Gly Asp Ser Pro
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Ile Thr Ser Arg Gly Asp His Gly Glu
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

Pro Pro Gly Arg Gly Asp Asn Gly Gly
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Ser Thr Asp Arg Gly Asp Ala Ser Ala
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic peptide

<400> SEQUENCE: 59

Leu Asn Pro Arg Gly Asp Ala Asn Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Pro Thr Thr Arg Gly Asp Cys Pro Asp
1               5
```

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide

<400> SEQUENCE: 61

Pro Gly Gly Arg Gly Asp Ser Ala Tyr
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Pro His Asp Arg Gly Asp Ala Gly Val
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Ala Ser Gly Arg Gly Asp Gly Gly Val
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Pro Ala Ser Arg Gly Asp Ser Pro Pro
1               5

<210> SEQ ID NO 65
<211> LENGTH: 5
<212> TYPE: PRT
<213> ORGANISM: H. sapiens

<400> SEQUENCE: 65

Val Pro His Thr Arg
1               5

<210> SEQ ID NO 66
<211> LENGTH: 10
<212> TYPE: PRT
<213> ORGANISM: H. sapiens

<400> SEQUENCE: 66

Cys Gln Ile Lys His His Asn Tyr Leu Cys
1               5                   10

<210> SEQ ID NO 67
<211> LENGTH: 12
<212> TYPE: PRT

```
<213> ORGANISM: H. sapiens

<400> SEQUENCE: 67

Trp Gln Pro Asp Thr Ala His His Trp Ala Leu Thr
 1               5                  10

<210> SEQ ID NO 68
<211> LENGTH: 10
<212> TYPE: PRT
<213> ORGANISM: H. sapiens

<400> SEQUENCE: 68

Cys Thr Thr His Trp Gly Phe Thr Leu Cys
 1               5                  10

<210> SEQ ID NO 69
<211> LENGTH: 14
<212> TYPE: PRT
<213> ORGANISM: Artificial Sequence
<220> FEATURE:
<223> OTHER INFORMATION: Synthetic peptide

<400> SEQUENCE: 69

Gly Ser Thr Ser Gly Ser Gly Lys Ser Ser Glu Gly Lys Gly
 1               5                  10

<210> SEQ ID NO 70
<211> LENGTH: 7
<212> TYPE: PRT
<213> ORGANISM: H. sapiens

<400> SEQUENCE: 70

Ile Lys Pro His Gln Gly Gln
 1               5
```

POLYPEPTIDES TARGETING VASCULAR ENDOTHELIAL GROWTH FACTOR RECEPTOR-2 AND ALPHA V BETA 3 INTEGRIN

This application is a continuation application of U.S. patent application Ser. No. 13/145,059, filed Oct. 4, 2011, now U.S. Pat. No. 8,741,839, which claims the benefit of National Stage Application No. PCT/US10/21332, filed Jan. 18, 2010, which claims the benefit of U.S. Provisional Application 61/145,579, filed on Jan. 18, 2009, all of which are incorporated herein by reference in their entirety.

FIELD OF THE INVENTION

The present invention relates to the field of angiogenesis-related diseases and their diagnosis, characterization and treatment.

BACKGROUND OF THE INVENTION

Angiogenesis, the process of new blood vessel formation from preexisting vasculature, plays critical roles in both normal physiological processes such as wound healing, pregnancy, tissue regeneration and in the pathogenesis of cancer, rheumatoid arthritis, and diabetic microvascular disease (see Carmeliet P (2005), Nature 438, pp. 932-936), and is regulated by a large number of pro- and antiangiogenic cytokines and growth factors (Ferrara N (2000), Curr Opin Biotechnol 11, pp. 617-624). During adulthood, most blood vessels remain quiescent and angiogenesis occurs only in the cycling ovary and in the placenta during pregnancy.

However, when angiogenic growth factors are produced in excess of angiogenesis inhibitors, endothelial cells are stimulated to proliferate. A number of angiogenic growth factors have been described to date among which vascular endothelial growth factor (VEGF) appears to play a key role as a positive regulator of physiological and pathological angiogenesis (Brown et al. (1997) in "Control of Angiogenesis" (Goldberg and Rosen, eds.), Birkhauser, Basel, pp. 233-269; Thomas K A (1996), J Biol Chem 271, pp. 603-606; Neufeld et al. (1999), FASEB J 13, pp. 9-22).

The focus on inhibition of angiogenesis for treatment of cancer and macular degeneration has largely focused on targeting vascular endothelial growth factor (VEGF) and its receptors due to the prominent role of this pathway in vascular formation. VEGF-mediated signaling is mediated through its interactions with two receptor tyrosine kinases, VEGFR1 (Flt-1) and VEGFR2 (Flk-1 or KDR). VEGFR2, which is expressed in vascular endothelial cells, monocytes, macrophages, and hematopoietic stem cells, is the primary mediator of the mitogenic and angiogenic effects of VEGF. VEGF is a homodimeric ligand that binds two molecules of VEGFR2, one at each pole, thereby triggering receptor dimerization and activation, with a $K_D$ of around 100 pM. The role of VEGFR1 is less clear, but it appears to function as a 'decoy' receptor that negatively regulated VEGF signaling by preventing VEGF from binding VEGFR2. VEGF-A is the main ligand for VEGFR2, but proteolytically cleaved forms of VEGF-C and VEGF-D may also bind to and activate VEGFR2. Hence, it may be beneficial to target VEGFR2 directly in order to best inhibit angiogenic processes.

Integrins are a diverse class of heterodimeric ($\alpha/\beta$) receptors involved in cell adhesion to extracellular matrix ligands. In particular, integrin $\alpha v\beta 3$ has been implicated as critically involved in tumor proliferation, metastasis, and angiogenesis, and there have therefore been many efforts to develop anti-cancer therapies that target integrin $\alpha v\beta 3$. Interestingly, there may be a critical link between integrin $\alpha v\beta 3$ and VEGF2-stimulated angiogenesis. Moreover, cross-talk and synergy exists between integrins and growth factor receptors. In particular, engagement of $\alpha v\beta 3$ integrin on endothelial cells promotes phosphorylation and activation of VEGFR2, thereby augmenting the mitogenic activity of VEGF. It has been shown that $\beta 3$ binds to VEGFR2 to potentiate its activity, and that $\alpha v\beta 3$ antagonists decrease the $\beta 3$-VEGFR2 interactions and VEGFR2 activation (though not VEGFR2 expression levels). These studies suggest that VEGFR2-mediated angiogenesis is potentiated by integrin $\alpha v\beta 3$.

Numerous other factors are involved in angiogenic processes, including transforming growth factors alpha and beta (TGF-$\alpha$ and -$\beta$), tumor necrosis factor (TNF), and fibroblast growth factor (FGF). Accordingly, blocking of single angiogenic molecules may have only modest effect on slowing tumor growth because there multiple angiogenesis pathways that can replace VEGF as the cancer progresses. Thus, there has been considerable interest in developing biological agents capable of binding to more than one set of ligand-receptor interactions in order to more efficiently block angiogenic processes.

PUBLICATIONS

Siemeister et al. (1998) "An antagonistic vascular endothelial growth factor (VEGF) variant inhibits VEGF-stimulated receptor autophosphorylation and proliferation of human endothelial cells", Proc Natl Acad Sci USA 95, pp. 4625-4629 and Boesen et al. (2002) "Single-chain vascular endothelial growth factor variant with antagonist activity", J Biol Chem 277 (43), pp. 40335-40341, disclose the preparation of a single-chain VEGF variants.

WO02081520 by Thomas P. Boesen and Torben Halkier, filed Apr. 8, 2002, and entitled "Single Chain Dimeric Polypeptides", discloses a single-chain dimeric polypeptide which binds to an extracellular ligand-binding domain of VEGFR2 or VEGFR3 receptor and which functions as a receptor antagonist for prevention or treatment of a disease or condition involving increased signal transduction from or increased activation of the VEGFR2 and/or VEGFR3 receptor, e.g. to inhibit angiogenesis or lymphangiogenesis. See also Ferrara et al. (2003) Nature Medicine 9:669-676; Ferrara and Kerbal. (2005) Nature 438:967-974; Meyer et al. (2006) Current Pharmaceutical Design 12:2723-2747; Silverman et al. (2009) Journal of Molecular Biology 385:1064-1075; Richards et al. (2003) Journal of Molecular Biology 326:1475-1488; Boesen et al. (1998) Proceedings of the National Academy of Sciences 95:4625-4629; Kiba et al. (2003) Journal of Biological Chemistry 278:13453-13461.

SUMMARY OF THE INVENTION

Compositions are provided of single-chain antagonistic human VEGF variants. The single-chain VEGF variants of the invention bind to VEGF receptors, including VEGFR2 receptors, but do not induce receptor activation, thereby antagonizing VEGF-stimulated receptor autophosphorylation and proliferation of endothelial cells. Compositions include the polypeptide or polypeptides of the invention, which may be provided as a single species or as a cocktail of two or more polypeptides, usually in combination with a pharmaceutically acceptable excipient. Compositions also include nucleic acids encoding such polypeptides. In some embodiments the polypeptide of the invention is conjugated to a functional moiety, e.g. a detectable label such a fluorescent label, a detectable label such as an isotopic label; a cytotoxic moiety, and the like, which may find use in imaging, quantitation, therapeutic purposes, etc.

In some embodiments the polypeptide of the invention is a single-chain antagonistic human VEGF variant having increased affinity for the VEGFR2, relative to the native polypeptide. Such polypeptides include without limitation those set forth in SEQ ID NO:10-18.

In some embodiments the polypeptide of the invention is a bifunctional single-chain antagonistic human VEGF variant comprising a native VEGF sequence, an amino acid linker, and a modified VEGF, where the modified VEGF comprises a loop with an integrin-recognition RGD sequence capable of binding αvβ3 integrin. Such polypeptides include without limitation those set forth in SEQ ID NO:5-8. Such polypeptides also include any polypeptide of SEQ ID NO:9-18, further comprising the modification of replacing amino acid residues of loop 2 or loop 3 in the mutated VEGF pole with an RGD motif, which RGD motif includes, without limitation XXRGDXXXX, XXXRGDXXX, or XXXXRGDXX. Specific RGD motifs of interest include those set forth in SEQ ID NO:29-SEQ ID NO:64. The RGD motif may be screened for binding to an αvβ3 integrin, an αvβ5 integrin, an α5β1 integrin, etc. In some embodiments the loop 3 sequence (SEQ ID NO:70) IKPHQGQ is replaced with the RGD motif. In other embodiments a motif for binding to a vascular protein other than αvβ3 integrin is provided in the scVEGF.

In some embodiments the polypeptide of the invention is a bifunctional single-chain antagonistic human VEGF variant having increased affinity for the VEGFR2, relative to the native polypeptide.

Methods are provided that utilize the polypeptides of the invention for imaging normal tissue, abnormal tissue, precancerous tissue, cancer, and tumors. In other embodiments methods are provided for diagnosis of precancerous tissue, cancer, and tumors. In other embodiments the bifunctional single-chain antagonistic VEGF variant of the invention is used in the treatment of an individual having a vascularized tumor or cancer.

BRIEF DESCRIPTION OF THE DRAWINGS

The accompanying drawings illustrate embodiments of the invention and, together with the description, serve to explain the invention. These drawings are offered by way of illustration and not by way of limitation.

DETAILED DESCRIPTION OF THE EMBODIMENTS

Figure 1:
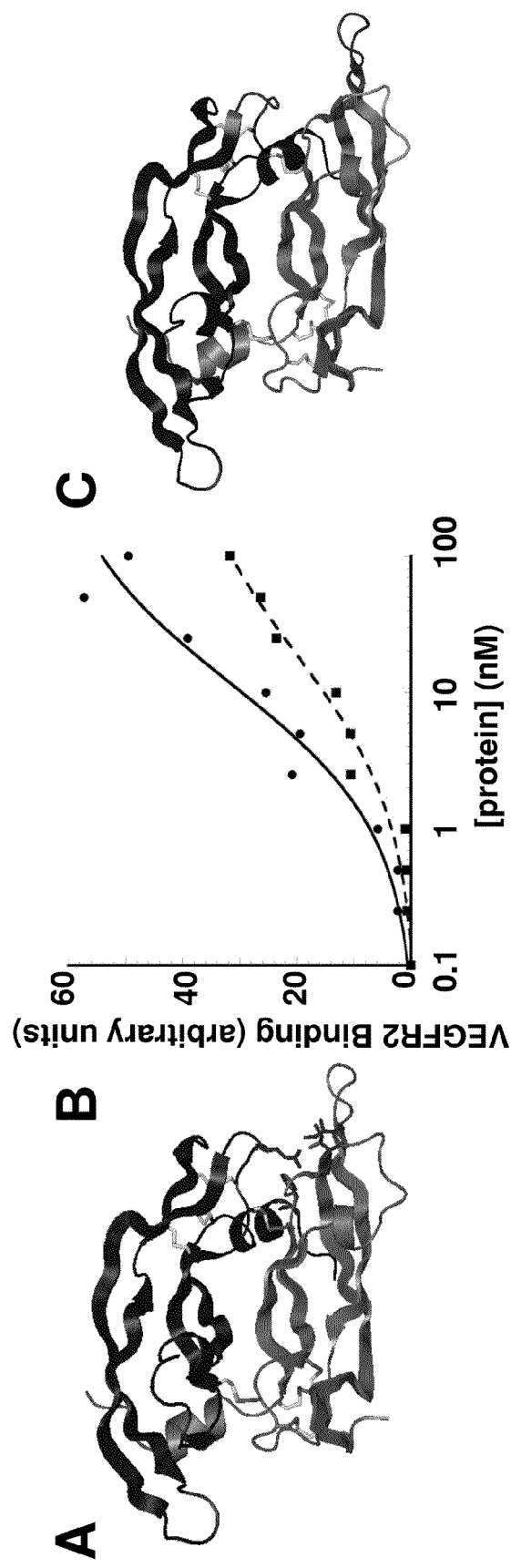
FIG. 1. Design of scVEGF and binding of yeast-displayed wt and mut variants. (A) Structure of VEGF. Chains 1 and 2 are shown in dark blue and light blue, respectively. Mutations in scVEGFmut are shown in red. (B) Binding of scVEGFwt (●) and scVEGFmut (■) to recombinant human VEGFR2 extracellular domain. (C) Loops subjected to saturation mutagenesis in scVEGFmut are shown. Loop 1, pink; loop 2, green; loop 3, red. Since it is difficult to determine which residues constitute the start and end of these loops (only loop 1 is disulfide constrained), multiple different amino acid registers were substituted for each loop.

VEGFR2 and αvβ3 integrin are critical effectors of tumor angiogenesis with broad clinical utility for the early detection of many solid cancers. Therapeutic and diagnostic agents that selectively inhibit or antagonize VEGFR2 as well as αvβ3 integrin are beneficial for treating angiogenesis-related disorders, in particular neoplasia and tumor metastasis. In addition to cancer, other proliferative diseases characterized by excessive neovascularization, e.g. psoriasis, age-related macular degeneration, diabetic retinopathy, rheumatoid arthritis, and the like, are treated with an effective dose of polypeptides of the invention, where the dose is effective at inhibiting angiogenesis.

DEFINITIONS

"VEGF" is a secreted disulfide-linked homodimer that selectively stimulates endothelial cells to proliferate, migrate, and produce matrix-degrading enzymes, all of which are processes required for the formation of new vessels. In addition to being the only known endothelial cell specific mitogen, VEGF is unique among angiogenic growth factors in its ability to induce a transient increase in blood vessel permeability to macromolecules. The term "VEGF" as used herein refers to proteins that are also known in the literature as "VEGF-A", i. e. the VEGF isoforms containing 121, 145, 165, 189 or 206 amino acid residues as described herein, in contrast to "VEGF-C" and "VEGF-D".

The human VEGF gene is organized in eight exons, separated by seven introns. Alternative exon splicing of the VEGF gene results in the generation of at least five different molecular species, having respectively 121, 145, 165, 189 and 206 amino acids (VEGF-121, VEGF-145, VEGF-165, VEGF-189, VEGF-206); these isoforms differ not only in their molecular weight but also in their biological properties, such as the ability to bind to cell surface heparin sulfate proteoglycans. VEGF-165 is the predominant molecular species produced by a variety of normal and transformed cells (Houck et al. (1991), Mol Endocrinol 5, pp. 1806-1814; Carmeliet et al. (1999), Nature Med 5, pp. 495-502).

VEGF signaling is mediated largely via two homologous, endothelium-specific tyrosine kinase receptors, VEGFR1 (Flt-1 aka fms-like tyrosine kinase 1) and VEGFR2 (Flk-1/KDR aka kinase domain receptor) whose expression is highly restricted to cells of endothelial origin (de Vries et al. (1992), Science 255, pp. 989-991; Millauer et al. (1993), Cell 72, pp. 835-846; Terman et al. (1991), Oncogene 6, pp. 519-524). Both receptors have an extracellular domain consisting of seven IgG-like domains, a transmembrane domain and an intracellular tyrosine kinase domain. The affinity of VEGFR1 for VEGF (Kd=1-20 pM) is higher compared to that of VEGFR2 (Kd=50-770 pM) (Brown et al. (1997) in "Control of Angiogenesis" (Goldberg and Rosen, eds.), Birkhauser, Basel, pp. 233-269; de Vries et al. (1992), Science 255, pp. 989-991; Terman et al. (1992) Biochem Biophys Res Commun 187, pp. 1579-1586).

While VEGFR1 is essential for physiologic and developmental angiogenesis, VEGFR2 is the major mediator of the mitogenic, angiogenic and permeability-enhancing effects of VEGF and, thus, a major factor in tumor angiogenesis; as a consequence, VEGFR2 overexpression can be observed on tumor endothelial cells of angiogenic vessels in many cancers (Tucker G C (2006), Curr Oncol Rep 8, pp. 96-103; Parker et al. (2005), Protein Eng Des Sel 18, pp. 435-44; Boesen et al. (2002), J Biol Chem 277, pp. 40335-41; Siemeister et al. (1998), Proc Natl Acad Sci USA 95, pp. 4625-9; Cai et al. (2005), Biotechniques 39, pp. S6-S17; Haubner R (2006), Eur J Nucl Med Mol Imaging 33 Suppl 1, pp. 54-63).

The term "scVEGF" as used herein describes a single-chain variant of VEGF, particularly a single chain in which two "poles" of VEGF are joined by a linker. For the purposes of the present invention the scVEGF is usually an antagonistic variant, as known in the art. Of particular relevance is the study by Boesen, et al., supra., in which a single-chain variant of VEGF121 (a common isoform of VEGF-A that does not require heparin binding like the larger isoform VEGF165 is prepared by linking the C-terminus of chain 1 to the N-terminus of chain 2 by a 14-amino acid flexible linker. In addition, mutations are added to both chains at one pole of the ligand in order to prevent binding of VEGFR2 at one receptor-binding site. The result is a protein that can bind only a single molecule of VEGFR2, and is antagonistic because it prevents receptor dimerization and activation.

The VEGF dimer contains two receptor binding interfaces lying on each pole of the molecule. Each of the two binding interfaces is typically able to contact one receptor monomer (either VEGFR1 or VEGFR2), thereby inducing receptor dimerization and activation. Consequently, an asymmetric VEGF variant that contains only one receptor binding interface at one pole of the dimer should not be able to induce receptor dimerization and activation and, therefore, act as a VEGF antagonist (Siemeister et al. (1998), Proc Natl Acad Sci USA 95, pp. 4625-4629).

In certain embodiments the polypeptide of the invention is a bifunctional single-chain antagonistic human VEGF variant comprising a native VEGF sequence, an amino acid linker, and a modified VEGF, where the modified VEGF comprises a loop with an inserted motif that binds to a vascular protein, which protein may include integrins such as $\alpha v\beta 3$ integrin, $\alpha v\beta 5$, $\alpha 5\beta 1$, etc., but may also include other vascular targets, e.g. including prostate membrane specific antigen (PMSA), PSA, MMPs, PDGFR, PDGF, and the like. Such polypeptides include without limitation any of the scVEGF polypeptides set forth herein, which further comprise the modification of replacing amino acid residues of loop 2 or loop 3 in the mutated VEGF pole with candidate motif. The binding motif may be a peptide sequence known in the art or may be designed through directed evolution, where a random or semi-random assortment of sequences is inserted into a permissive loop and screened for binding. In some embodiments the loop 3 sequence (SEQ ID NO:70) IKPHQGQ is replaced with the motif. Binding of the modified polypeptide to a target may be determined by various methods, including selective binding to purified protein, cell lines, tissues including sections of tumor tissue, and the like.

Specific targets and motifs of interest include prostate specific membrane antigen, which is a transmembrane glycoprotein homodimer expressed almost exclusively in prostatic epithelial cells (O'Keefe D S, Prostate, 2004). Both expression and enzymatic activity of PSMA are elevated in prostate cancer and in the neovasculature of many solid tumors, with expression levels closely correlated with disease grade (Lapidus R G, Prostate, 2000). Interestingly, endothelial cells of the neovasculature of almost all solid tumors express PSMA but not cells in the neovasculature associated with normal tissues (Silver D A, Clin Cancer Res 1997). In particular, there is an increase in both expression and enzymatic activity of PSMA in aggressive prostate tumors. The highest levels of PSMA expression are associated with high-grade, hormone-refractory and metastatic prostate cancer (Kawakami M, Cancer Res., 1997). In fact, PSMA mRNA is upregulated upon androgen withdrawal (Israeli R S, Cancer Res., 1994). In general, PSMA expression is ubiquitous, with expression in nearly all tumor sites. These properties have made PSMA an ideal target for developmental prostate cancer imaging agents and therapeutics, especially in advanced disease.

PSMA has both glutamate carboxypeptidase II activity that cleaves $\alpha$-linked glutamate from N-acetylaspartyl glutamate (NAALADase activity) and $\gamma$-linked glutamates from polyglutamated folates sequentially (folate hydrolase activity). Although its mechanism in not yet known, PSMA (a folate hydrolase) may facilitate prostate carcinogenesis by enhancing the proliferative and invasive capability of prostate cancer cells (which can be blocked by folic acid). It will be interesting to use peptides that bind PSMA and can/cannot inhibit its enzymatic activity in order to investigate if enzymatic activity contributes to the initiation of prostate carcinogenesis. It will also be interesting to see whether the active peptides will be able to block PSMA dimerization, which is dependent upon the presence of zinc ions in the active site of PSMA and is required for PSMA's enzymatic activity. This can be done using a purified ecto domain of PSMA which is able to dimerize (Lupoid S E, Mol Cancer Ther, 2004).

A stringent phage display strategy with a fusion protein containing only the extracellular portion of PSMA (containing two amino-terminal affinity tags), was applied to identify potential PSMA binding peptides. Alignment revealed some weakly similar peptide sequences, providing the consensus SEQ ID NO:65 VPHTR (Lupoid S E, Mol Cancer Ther, 2004). The most active peptide SEQ ID NO:66 (CQIKHHNYLC) was able to bind purified PSMA (10 µM range), stabilize the protein to enhance enzymatic activity, and target phage to prostate cancer cells (LNCaP).

Linear peptides: In another study, a random phage library produced a linear peptide dimer SEQ ID NO:67 (WQPDTAHHWALT) with selective affinities to prostate cancer cells expressing PSMA (LNCaP and CWR22R) vs. PSMA deficient cells. The peptide also had selective affinity to purified PSMA and ability to inhibit PSMA enzymatic activity (also in the µM range) (Aggarwal S, Cancer Res., 2006). This dihistidine peptide motif had also emerged as part of a consensus PSMA-binding sequence (i.e., SEQ ID NO:66 CQKHHNYLC) as mentioned above (Lupoid S E, Mol Cancer Ther, 2004). An interesting question to address will be whether the presence of histidines, which are known to chelate divalent metal ions including zinc (found in the PSMA catalytic binding site), may lead to inactivation of the enzyme and whether it depends on the sequence that surrounds them, which results in a specific fold that they adopt.

Other targets of interest include Matrix Metalloproteinases (MMPs). Tumor growth, angiogenesis, and metastasis are dependent on MMP activity. However, the lack of inhibitors specific for the type IV collagenase/gelatinase family of MMPs has thus far prevented the selective targeting of MMP-2 (gelatinase A) and MMP-9 (gelatinase B) for therapeutic intervention in cancer. Koivunan et al. (Koivunen E, Nature Biotechnology, 1999) used libraries of random peptides to isolate selective gelatinase inhibitors. They identified a class of cyclic peptides containing an HWGF motif that are specific inhibitors of MMP-2 and MMP-9. Specifically, the cyclic decapeptide SEQ ID NO:68 CTTHWGFTLC was able to (i) inhibit the activities of these enzymes, (ii) suppress migration of both tumor cells and endothelial cells in vitro, (iii) home to tumor vasculature in vivo, and (iv) prevent the growth and invasion of tumors in mice. SEQ ID NO:68 CTTHWGFTLC-displaying phage was also able to specifically target angiogenic blood vessels in vivo.

"Integrins" are a family of cell surface adhesion receptors that non-covalently associate into α/β heterodimers with distinct ligand binding specificities and cell signaling properties (Giancotti & Ruoslahti (1999), Science 285, pp. 1028-32). As cell surface adhesion receptors, integrins are involved in the attachment of cells to matrix via RGD peptide sequences; in addition, they function as receptors for transmitting signals important for cell migration, invasion, proliferation, and survival. In their roles as major adhesion receptors, integrins signal across the plasma membrane in both directions. At least six integrin inhibitors on endothelial cells are being evaluated in clinical trials for cancer (Tucker (2006), Curr Oncol Rep 8, pp. 96-103) with αvβ3 (also known as the vitronectin receptor) being the most abundant and influential receptor regulating angiogenesis (Shattil & Ginsberg (1997), J Clin Invest 100, pp. S91-S95).

There are several manifestations of a tightly collaborative relationship between integrins and receptors for growth factors (Ross (2004), Cardiovasc Res 63, pp. 381-390). On endothelial cells, engagement of αvβ3 integrin promotes phosphorylation and activation of vascular endothelial growth factor (VEGF) receptor (VEGFR)-2, thereby augmenting the mitogenic activity of VEGFs (Soldi et al. (1999), EMBO J 18, pp. 882-892). While αvβ3 integrins are highly expressed on activated endothelial cells in tumor neovasculature, they are only weakly expressed in resting endothelial cells and most normal tissues and organs (Brooks et al. (1994), Science 264, pp. 569-71; Brooks et al. (1994), Cell 79, pp. 1157-64). The terms "avb3", "alpha v beta 3" and "αvβ3" are used interchangeably throughout the text.

RGD Peptides.

It has been demonstrated that the αvβ3 integrin binds to a number of Arg-Gly-Asp (RGD) containing matrix molecules, such as fibrinogen (Bennett et al. (1983), Proc Natl Acad Sci USA 80, p. 2417), fibronectin (Ginsberg et al. (1983), J Clin Invest 71, pp. 619-624), and von Willebrand factor (Ruggeri et al. (1982), Proc Natl Acad Sci USA 79, p. 6038). Compounds containing the RGD sequence mimic extracellular matrix ligands so as to bind to cell surface receptors.

While it has been fairly straightforward to insert RGD motifs into linear or cyclic peptide libraries and screen for integrin binders with micromolar affinities, generation of peptides that bind with therapeutically relevant concentrations (low nanomolar) or high specificities to particular integrins require that the RGD sequence is appropriately positioned for binding the integrin of interest. Like natural integrin ligands, the affinities and specificities of these RGD-containing peptides and proteins are largely dependent on the orientation of the Arg and Asp residues, as well as the conformation of the RGD loop, which is dictated by the amino acids flanking the RGD sequence. Rigidifying the RGD motif by backbone cyclization or placing it within a disulfide-bonded loop can improve integrin-binding affinity and specificity (Silverman et al. (2009), J Mol Biol 385, pp. 1064-1075.

The term "domain" as used herein describes a discrete portion of a protein assumed to fold independently of the rest of the protein and possessing its own function. The term "single domain" as used herein describes the presence of one domain in a protein.

The terms "polypeptide" and "polypeptides" as used herein include proteins and fragments thereof. Polypeptides are disclosed herein as amino acid residue sequences. Those sequences are written left to right in the direction from the amino to the carboxy terminus or N to C terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "variant" refers to a polypeptide or protein that differs from a reference polypeptide or protein, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. The term "identical or essentially similar single-chain VEGF variants" as used herein include variants having more than 50% sequence identity to the single-chain VEGF variants disclosed in embodiments of the present invention.

The terms "mutant" and "clone" are employed broadly to refer to a protein that differs in some way from a reference wild-type protein, where the protein may retain biological properties of the reference wild-type (e.g., naturally occurring) protein, or may have biological properties that differ from the reference wild-type protein. For the purposes of the invention reference may be made to a "modified VEGF receptor binding site", which differs in amino acid sequence from the native polypeptide but which retains properties of interest. The term "biological property" of the subject proteins includes, but is not limited to, biological interactions in cancer and/or ischemic or hypoxic related diseases, in vivo and/or in vitro stability (e.g., half-life), and the like. Mutants and clones can include single amino acid changes (point mutations), deletions of one or more amino acids (point-deletions), N-terminal truncations, C-terminal truncations, insertions, and the like. Mutants and clones can be generated using standard techniques of molecular biology.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are herein described.

Modifications and changes can be made in the structure of the polypeptides and proteins of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's or protein's biological functional activity, certain amino acid sequence substitutions can be made in a polypeptide or protein sequence and nevertheless obtain a polypeptide or protein with like properties.

Amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure, therefore, consider functional or biological equivalents of a polypeptide or protein as set forth above. In particular, embodiments of the polypeptides and proteins can include variants having about 50%, 60%, 70%, 80%, 90%, and 95% sequence identity to the polypeptide and protein of interest.

"Identity," as known in the art, is a relationship between two or more polypeptide or protein sequences, as determined by comparing the sequences. In the art, "identity" also refers to the degree of sequence relatedness between polypeptides or proteins, as determined by the match between strings of such sequences. "Identity" can be readily calculated by known bioinformational methods.

Polypeptide Compositions

Provided herein are compositions and methods related to single-chain variants of VEGF, including bifunctional proteins targeting both VEGFR2 and αvβ3 integrin, effectively antagonizing their activation and so exerting anti-angiogenic effects. As single-chain antagonistic VEGF variants with one intact VEGF receptor binding site at the one pole and one mutated VEGF receptor binding site at the other pole, these proteins bind to VEGF receptors, in particular to VEGFR2 receptors, but fail to induce receptor activation, thereby antagonizing VEGF-stimulated receptor autophosphorylation and proliferation of endothelial cells. In addition, single-chain antagonistic VEGF variants may comprise a loop carrying an integrin-recognition RGD sequence for binding of αvβ3 integrin in the mutated receptor binding site, thereby antagonizing not only VEGF-stimulated receptor autophosphorylation and proliferation of endothelial cells, but also the activation of alpha v beta 3 integrin.

Since VEGFR1 and VEGFR2 belong to the class of oligomeric cellular receptors that depend on oligomerization and/or conformational changes to be activated, binding of the single-chain variants of the present invention without activation of the receptors allows the single-chain variants to function as effective antagonists of VEGF and VEGF-mediated phosphorylation and stimulation of endothelial cells.

Embodiments of the invention describe the preparation of such bifunctional, single-chain VEGF variants and their use in molecular cancer imaging and treatment of cancer, age-related macular degeneration, diabetic retinopathy, rheumatoid arthritis and psoriasis.

Single-chain antagonistic VEGF protein variants were engineered from the monomer VEGF-121, but contain only the 97-amino acid core region of VEGF-121, and have truncated N- and C-termini relative to VEGF-121. These variants have one intact and one mutated VEGF receptor binding sites, where the mutated binding site contains a loop with an integrin-recognition RGD sequence for binding of alpha v beta 3 integrin. The single-chain VEGF variants bind to VEGF receptors, in particular to VEGFR2 receptors, but fail to induce receptor activation, thereby antagonizing VEGF-stimulated receptor autophosphorylation and proliferation of endothelial cells.

An exemplary single chain variant of VEGF comprises two chains of the 97-amino acid core region of VEGF-121 (E13-D109). A flexible, amino acid linker links the C-terminus of chain 1 to the N-terminus of chain 2. An exemplary linker comprises the amino acid sequence SEQ ID NO:69 GSTSGSGKSSEGKG, however many such linkers are known and used in the art and may serve this purpose. The polypeptides of the invention are typically provided in single-chain form, which means that the monomers are linked by peptide bonds through a linker peptide, rather than being linked by noncovalent bonds or disulfide bonds. Optionally Chain 1 has F17A and E64A mutations in the VEGFR2 recognition region. Chain 2 may be mutated to abolish binding to VEGFR2, including without limitation an I46A mutation, I83A mutation, etc.

In some embodiments the polypeptide of the invention is a single-chain antagonistic human VEGF variant having increased affinity for the VEGFR2, relative to the native polypeptide. Such polypeptides include without limitation those set forth in SEQ ID NO:10-18.

In some embodiments the polypeptide of the invention is a bifunctional single-chain antagonistic human VEGF variant comprising a native VEGF sequence, an amino acid linker, and a modified VEGF, where the modified VEGF comprises a loop with an integrin-recognition RGD sequence capable of binding αvβ3 integrin. Such polypeptides include without limitation those set forth in SEQ ID NO:5-8. Such polypeptides also include any polypeptide of SEQ ID NO:9-18, further comprising the modification of replacing amino acid residues of loop 3 in the mutated VEGF pole with an RGD motif, which RGD motif includes, without limitation XXRGDXXXX, XXXRGDXXX, or XXXXRGDXX, where X is any amino acid. Specific RGD motifs of interest include those set forth in SEQ ID NO:29-SEQ ID NO:64. In some embodiments the loop 3 sequence (SEQ ID NO:70) IKPHQGQ (I83-Q89) is replaced with the RGD motif.

In some embodiments the polypeptide of the invention is a bifunctional single-chain antagonistic human VEGF variant having increased affinity for the VEGFR2, relative to the native polypeptide.

Table 1 shows all of the sequences of the integrin-binding loop peptides utilized in the polypeptides of the invention.

|  | Grafted Loop Sequence |
|---|---|
| SEQ ID NO: 29 | PFGTRGDSS |
| SEQ ID NO: 30 | SGERGDGPT |
| SEQ ID NO: 31 | SDGRGDGSV |
| SEQ ID NO: 32 | PIGRGDGST |
| SEQ ID NO: 33 | LAERGDSSS |
| SEQ ID NO: 34 | PTGRGDLGA |
| SEQ ID NO: 35 | RGIRGDSGA |
| SEQ ID NO: 36 | VGGRGDVGV |
| SEQ ID NO: 37 | ITARGDSFG |
| SEQ ID NO: 38 | ITERGDSGH |
| SEQ ID NO: 39 | PQARGDRSD |
| SEQ ID NO: 40 | SRTRGDASD |
| SEQ ID NO: 41 | PAARGDGGL |
| SEQ ID NO: 42 | PVARGDSGA |
| SEQ ID NO: 43 | PQQRGDGPH |
| SEQ ID NO: 44 | PLPRGDGQR |
| SEQ ID NO: 45 | HAGRGDSPS |
| SEQ ID NO: 46 | TSLRGDTTW |
| SEQ ID NO: 47 | PNFRGDEAY |
| SEQ ID NO: 48 | AGVPRGDSP |
| SEQ ID NO: 49 | PRSTRGDST |
| SEQ ID NO: 50 | PFGVRGDDN |
| SEQ ID NO: 51 | GFPFRGDSPAS |
| SEQ ID NO: 52 | PSVRRGDSPAS |
| SEQ ID NO: 53 | PFAVRGDRP |
| SEQ ID NO: 54 | PWPRRGDLP |
| SEQ ID NO: 55 | PSGGRGDSP |
| SEQ ID NO: 56 | ITSRGDHGE |
| SEQ ID NO: 57 | PPGRGDNGG |
| SEQ ID NO: 58 | STDRGDASA |
| SEQ ID NO: 59 | LNPRGDANT |
| SEQ ID NO: 60 | PTTRGDCPD |
| SEQ ID NO: 61 | PGGRGDSAY |
| SEQ ID NO: 62 | PHDRGDAGV |
| SEQ ID NO: 63 | ASGRGDGGV |
| SEQ ID NO: 64 | PASRGDSPP |

Modifications and changes can be made in the selection of the monomers used (VEGF-121, VEGF-145, VEGF-165, VEGF-189 and VEGF-206), in the length of the core region of VEGF and/or in the length of the linker yielding identical or essentially similar single-chain VEGF variants with like properties as for the single-chain VEGF variants described in embodiments of the present invention.

Polypeptides can be produced through recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity.

The polypeptides may be produced by recombinant DNA technology using techniques well known in the art. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

Typically, the coding sequence is placed under the control of a promoter that is functional in the desired host cell to produce relatively large quantities of the gene product. An extremely wide variety of promoters are well-known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Expression can be achieved in prokaryotic and eukaryotic cells utilizing promoters and other regulatory agents appropriate for the particular host cell. Exemplary host cells include, but are not limited to, *E. coli*, other bacterial hosts, yeast, and various higher eukaryotic cells such as the COS, CHO and HeLa cells lines and myeloma cell lines.

The polypeptide may be labeled, either directly or indirectly. Any of a variety of suitable labeling systems may be used, including but not limited to, radioisotopes such as $^{125}$I; enzyme labeling systems that generate a detectable colorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by a Fab expression library.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)).

As an option to recombinant methods, polypeptides can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of polypeptides of the invention protein can be synthesized and then joined together. Methods for conducting such reactions are described by Grant (1992) Synthetic Peptides: A User Guide, W.H. Freeman and Co., N.Y.; and in "Principles of Peptide Synthesis," (Bodansky and Trost, ed.), Springer-Verlag, Inc. N.Y., (1993).

The polypeptides of the invention can be coupled or conjugated to one or more cytotoxic or imaging moieties. As used herein, "cytotoxic moiety" is a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. "Imaging moiety" (I) is a moiety that can be utilized to increase contrast between a tumor and the surrounding healthy tissue in a visualization technique (e.g., radiography, positron-emission tomography, single-photon emission computed tomography, near-infrared fluorescence imaging, magnetic resonance imaging, ultrasound, direct or indirect visual inspection). Thus, suitable imaging moieties include radiography moieties (e.g. heavy metals and radiation emitting moieties), positron emitting moieties, magnetic resonance contrast moieties, gas-filled mirobubble spheres for contrast-enhanced ultrasound, and optically visible moieties (e.g., fluorescent or visible-spectrum dyes, visible particles, etc.). It will be appreciated by one of ordinary skill that some overlap exists between therapeutic and imaging moieties. For instance $^{212}$Pb and $^{212}$Bi are both useful radioisotopes for therapeutic compositions, but are also electron-dense, and thus provide contrast for X-ray radiographic imaging techniques, and can also be utilized in scintillation imaging techniques.

In general, therapeutic or imaging agents may be conjugated to the polypeptides of the invention by any suitable technique, with appropriate consideration of the need for pharmokinetic stability and reduced overall toxicity to the patient. A therapeutic agent may be coupled to a polypeptide either directly or indirectly (e.g. via a linker group). A direct reaction between an agent and a polypeptide is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance a polypeptide from an agent in order to avoid interference with binding capabilities. A linker group can also serve to increase the chemical reactivity of a substituent on a moiety or a polypeptide, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the polypeptide moiety) and succinimidyl linkers (which react with a primary amine on the polypeptide moiety). Several primary amine and sulfhydryl groups are present on a polypeptide, and additional groups may be designed into recombinant molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic or imaging moieties may be coupled to the polypeptides of the invention through an oxidized carbohydrate group at a glycosylation site, as described in U.S. Pat. Nos. 5,057,313 and 5,156,840. Yet another alternative method of coupling a polypeptide to the cytotoxic or imaging moiety is by the use of a non-covalent binding pair, such as streptavidin/biotin, or avidin/biotin. In these embodiments, one member of the pair is covalently coupled to a polypeptide and the other member of the binding pair is covalently coupled to the cytotoxic or imaging moiety.

Carriers and linkers specific for radionuclide agents (both for use as cytotoxic moieties or positron-emission imaging moieties) include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. Such chelation carriers are also useful for magnetic spin contrast ions for use in magnetic resonance imaging tumor visualization methods, and for the chelation of heavy metal ions for use in radiographic visualization methods.

Preferred radionuclides for use as cytotoxic moieties are radionuclides that are suitable for pharmacological administration. Such radionuclides include $^{123}$I, $^{125}$I, $^{131}$I $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At may be conjugated to polypeptides of the invention for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and N-succinimidyl 5-[$^{131}$I]iodob-3-pyridinecarboxylate (SIPC). Any iodine isotope may be utilized in the recited iodo-reagents. Radionuclides can be conjugated to polypeptides of the invention by suitable chelation agents known to those of skill in the nuclear medicine arts.

Preferred radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Examples of such compositions, which may be utilized for x-ray radiography are described in U.S. Pat. No. 5,709,846, incorporated fully herein by reference. Such moieties may be conjugated to the polypeptides of the invention through an acceptable chemical linker or chelation carrier. In addition, radionuclides which emit radiation capable of penetrating the skull may be useful for scintillation imaging techniques. Suitable radionuclides for conjugation include $^{99}$Tc, $^{111}$In, and $^{67}$Ga. Positron emitting moieties for use in the present invention include $^{18}$F, which can be easily conjugated by a fluorination reaction with the polypeptides of the invention according to the method described in U.S. Pat. No. 6,187,284, or $^{64}$Cu, which can be conjugated through chemical chelators as extensively described in the literature.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred. Examples of such chelates, suitable for magnetic resonance spin imaging, are described in U.S. Pat. No. 5,733,522, incorporated fully herein by reference. Nuclear spin contrast chelates may be conjugated to the polypeptides of the invention through a suitable chemical linker.

Optically visible moieties for use as imaging moieties include fluorescent dyes, or visible-spectrum dyes, visible particles, and other visible labeling moieties. Fluorescent dyes such as ALEXA dyes, fluorescein, coumarin, rhodamine, bodipy Texas red, and cyanine dyes, are useful when sufficient excitation energy can be provided to the site to be inspected visually. Endoscopic visualization procedures may be more compatible with the use of such labels. For many procedures where imaging agents are useful, such as during an operation to resect a brain tumor, visible spectrum dyes are preferred. Acceptable dyes include FDA-approved food dyes and colors, which are non-toxic, although pharmaceutically acceptable dyes which have been approved for internal administration are preferred. In preferred embodiments, such dyes are encapsulated in carrier moieties, which are in turn conjugated to the polypeptides of the invention. Alternatively, visible particles, such as colloidal gold particles or latex particles, may be coupled to the polypeptides of the invention via a suitable chemical linker.

Pharmaceutical Formulations

Formulations of polypeptides of the invention find use in diagnosis and therapy. The formulation may comprise one, two or more polypeptides of the invention. The therapeutic formulation may be administered in combination with other methods of treatment, e.g. chemotherapy, radiation therapy, surgery, and the like.

Formulations may be optimized for retention and stabilization at a targeted site. Stabilization techniques include enhancing the size of the polypeptide, by cross-linking, multimerizing, or linking to groups such as polyethylene glycol, polyacrylamide, neutral protein carriers, etc. in order to achieve an increase in molecular weight. Other strategies for increasing retention include the entrapment of the polypeptide in a biodegradable or bioerodible implant. The rate of release of the therapeutically active agent is controlled by the rate of transport through the polymeric matrix, and the biodegradation of the implant. The transport of polypeptide through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. The polypeptide may be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Nucleic Acids

Nucleic acid sequences encoding polypeptides of the invention find use in the recombinant production of the encoded polypeptide, and the like. One of skill in the art can readily utilize well-known codon usage tables and synthetic methods to provide a suitable coding sequence for any of the polypeptides of the invention. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Methods of Use

Molecular imaging unites molecular biology and in vivo imaging. It enables the visualisation of the cellular function and the follow-up of the molecular process in living organisms without perturbing them.

In some embodiments, the methods are adapted for imaging use in vivo, e.g., to locate or identify sites where angiogenic cells are present. In these embodiments, a detectably-labeled polypeptide of the invention is administered to an individual (e.g., by injection), and labeled cells are located using standard imaging techniques, including, but not limited to, near-infrared fluorescence imaging, positron emission tomography, magnetic resonance imaging, computed tomography scanning, and the like.

For diagnostic in vivo imaging, the type of detection instrument available is a major factor in selecting a given radionuclide. The radionuclide chosen must have a type of decay that is detectable by a given type of instrument. In general, any conventional method for visualizing diagnostic imaging can be utilized in accordance with this invention. Another important factor in selecting a radionuclide for in vivo diagnosis is that its half-life be long enough that it is still detectable at the time of maximum uptake by the target tissue, but short enough that deleterious radiation of the host is minimized. A currently used method for labeling with $^{99m}$Tc is the reduction of pertechnetate ion in the presence of a chelating precursor to form the labile $^{99m}$Tc-precursor complex, which, in turn, reacts with the metal binding group of a bifunctionally modified chemotactic peptide to form a $^{99m}$Tc-chemotactic peptide conjugate. In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy (γ-ray) emissions of the specific isotopes employed and the sensitivity and sophistication of the instruments used to detect them, the two-dimensional distribution of radioactivity may be inferred from outside of the body. Among the most commonly used positron-emitting nuclides in PET are included $^{11}$C, $^{13}$N, $^{15}$O, and $^{18}$F, and $^{64}$Cu. Isotopes that decay by electron capture and/or γ emission are used in SPECT, and include $^{123}$I and $^{99m}$Tc, and $^{111}$In.

Therapeutic Methods

The dose of a polypeptide of the invention administered to a subject, particularly a human, in the context of the present invention should be sufficient to effect a therapeutic reduction in angiogenesis in the subject over a reasonable time frame. The dose will be determined by, among other considerations, the potency of the particular polypeptide of the invention employed and the condition of the subject, as well as the body weight of the subject to be treated. The size of the dose also will be determined by the existence, nature, and extent of any adverse side-effects that might accompany the administration of a particular compound.

In determining the effective amount of polypeptide in the reduction of angiogenesis, the route of administration, the kinetics of the release system (e.g., pill, gel or other matrix), and the potency of the agonist are considered so as to achieve the desired anti-angiogenic effect with minimal adverse side effects. The polypeptide of the invention will typically be administered to the subject being treated for a time period ranging from a day to a few weeks, consistent with the clinical condition of the treated subject.

As will be readily apparent to the ordinarily skilled artisan, the dosage is adjusted for polypeptide of the invention according to their potency and/or efficacy relative to a VEGF antagonist. A dose may be in the range of about 0.001 µg to 100 mg, given 1 to 20 times daily, and can be up to a total daily dose of about 0.01 µg to 100 mg. If applied topically, for the purpose of a systemic effect, the patch or cream would be designed to provide for systemic delivery of a dose in the range of about 0.01 µg to 100 mg. If injected for the purpose of a systemic effect, the matrix in which the polypeptide of the invention is administered is designed to provide for a systemic delivery of a dose in the range of about 0.001 µg to 1 mg. If injected for the purpose of a local effect, the matrix is designed to release locally an amount of polypeptide of the invention in the range of about 0.001 µg to 100 mg.

Regardless of the route of administration, the dose of polypeptide of the invention can be administered over any appropriate time period, e.g., over the course of 1 to 24 hours, over one to several days, etc. Furthermore, multiple doses can be administered over a selected time period. A suitable dose can be administered in suitable subdoses per day, particularly in a prophylactic regimen. The precise treatment level will be dependent upon the response of the subject being treated.

In some embodiments, a polypeptide of the invention is administered in a combination therapy with one or more other therapeutic agents, including an inhibitor of angiogenesis; and a cancer chemotherapeutic agent.

Suitable chemotherapeutic agents include, but are not limited to, the alkylating agents, e.g. Cisplatin, Cyclophosphamide, Altretamine; the DNA strand-breakage agents, such as Bleomycin; DNA topoisomerase II inhibitors, including intercalators, such as Amsacrine, Dactinomycin, Daunorubicin, Doxorubicin, Idarubicin, and Mitoxantrone; the nonintercalating topoisomerase II inhibitors such as, Etoposide and Teniposide; the DNA minor groove binder Plicamycin; alkylating agents, including nitrogen mustards such as Chlorambucil, Cyclophosphamide, Isofamide, Mechlorethamine, Melphalan, Uracil mustard; aziridines such as Thiotepa; methanesulfonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine; antimetabolites, including folate antagonists such as Methotrexate and trimetrexate; pyrimidine antagonists, such as Fluorouracil, Fluorodeoxyuridine, CB3717, Azacytidine, Cytarabine; Floxuridine purine antagonists including Mercaptopurine, 6-Thioguanine, Fludarabine, Pentostatin; sugar modified analogs include Cyctrabine, Fludarabine; ribonucleotide reductase inhibitors including hydroxyurea; Tubulin interactive agents including Vincristine Vinblastine, and Paclitaxel; adrenal corticosteroids such as Prednisone, Dexamethasone, Methylprednisolone, and Prodnisolone; hormonal blocking agents including estrogens, conjugated estrogens and Ethinyl Estradiol and Diethylstilbesterol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone estrogens, conjugated estrogens and Ethinyl Estradiol and Diethylstilbesterol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone; and the like.

The polypeptide of the invention may be administered with other anti-angiogenic agents. Anti-angiogenic agents include, but are not limited to, angiostatic steroids such as heparin derivatives and glucocorticosteroids; thrombospondin; cytokines such as IL-12; fumagillin and synthetic derivatives thereof, such as AGM 12470; interferon-α; endostatin; soluble growth factor receptors; neutralizing monoclonal antibodies directed against growth factors such as vascular endothelial growth factor; and the like.

The instant invention provides a method of reducing angiogenesis in a mammal. The method generally involves administering to a mammal a polypeptide of the invention in an amount effective to reduce angiogenesis. An effective amount of an polypeptide of the invention reduces angiogenesis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or more, when compared to an untreated (e.g., a placebo-treated) control.

Whether angiogenesis is reduced can be determined using any known method. Methods of determining an effect of an agent on angiogenesis are known in the art and include, but are not limited to, inhibition of neovascularization into implants impregnated with an angiogenic factor; inhibition of blood vessel growth in the cornea or anterior eye chamber; inhibition of endothelial cell proliferation, migration or tube formation in vitro; the chick chorioallantoic membrane assay; the hamster cheek pouch assay; the polyvinyl alcohol sponge disk assay. Such assays are well known in the art and have been described in numerous publications, including, e.g., Auerbach et al. ((1991) *Pharmac. Ther.* 51:1-11), and references cited therein.

The invention further provides methods for treating a condition or disorder associated with or resulting from pathological angiogenesis. In the context of cancer therapy, a reduction in angiogenesis according to the methods of the invention effects a reduction in tumor size; and a reduction in tumor metastasis. Whether a reduction in tumor size is achieved can be determined, e.g., by measuring the size of the tumor, using standard imaging techniques. Whether metastasis is reduced can be determined using any known method. Methods to assess the effect of an agent on tumor size are well known, and include imaging techniques such as computerized tomography and magnetic resonance imaging.

Any condition or disorder that is associated with or that results from pathological angiogenesis, or that is facilitated by neovascularization (e.g., a tumor that is dependent upon neovascularization), is amenable to treatment with a polypeptide of the invention.

Conditions and disorders amenable to treatment include, but are not limited to, cancer; atherosclerosis; proliferative retinopathies such as diabetic retinopathy, age-related maculopathy, retrolental fibroplasia; excessive fibrovascular proliferation as seen with chronic arthritis; psoriasis; and vascular malformations such as hemangiomas, and the like.

The instant methods are useful in the treatment of both primary and metastatic solid tumors, including carcinomas, sarcomas, leukemias, and lymphomas. Of particular interest is the treatment of tumors occurring at a site of angiogenesis. Thus, the methods are useful in the treatment of any neoplasm, including, but not limited to, carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). The instant methods are also useful for treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, the instant methods are useful for reducing metastases from the tumors described above either when used alone or in combination with radiotherapy and/or other chemotherapeutic agents.

Other conditions and disorders amenable to treatment using the methods of the instant invention include autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemangiomas, and capillary proliferation within atherosclerotic plaques; Osler-Webber Syndrome; plaque neovascularization; telangiectasia; hemophiliac joints; angiofibroma; and excessive wound granulation (keloids).

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, examples will be described to illustrate parts of the invention.

EXAMPLES

Example 1

Generation of Single-Chain VEGF Variant

We created a single-chain variant of VEGF (termed scVEGF) in which two monomeric VEGF chains were physically tethered through a flexible linker. Point mutations were introduced into scVEGF (chain 1: F17A, E64A; chain 2: I46A, I83A) that confer antagonistic activity by blocking a second molecule of VEGFR1 or VEGFR2 from binding (Boesen et al. (2002), J Biol Chem 277, pp. 40335-41; Siemeister et al. (1998), Proc Natl Acad Sci USA 95, pp. 4625-9; Fuh et al. (1998), J Biol Chem 273, pp. 11197-204). Once single-chain VEGF variants were established, a 9 amino-acid integrin binding loop was introduced into scVEGF in place of residues I83-Q89 (on chain 2), which in wild-type VEGF would normally allow binding a second molecule of VEGFR2.

Example 2

Single-Chain VEGF Antagonists Engineered to Bispecifically Target VEGFR2 and $\alpha_v\beta_3$ Integrin In this work, we used a single-chain VEGF (scVEGF) antagonist as a scaffold for engineering recognition to integrin $\alpha v\beta 3$. The mutated pole of scVEGF had one of the VEGFR2-recognition loops replaced with a loop containing RGD and randomized flanking residues. The library of scVEGFrgd variants was screened by yeast surface display, and proteins with high affinity for both receptors were selected. To enhance their potency at inhibiting VEGF-mediated processes we affinity-matured these scVEGF proteins against VEGFR2.

To evaluate the inhibitory action of these variants on the induction of angiogenesis, we examined their effect on the function of VEGF. Since VEGF has been shown to be the central positive regulator of the early growth of neovessels, and inhibition of VEGFR2 activity limits the ability of most tumors to stimulate the formation of blood vessels, we examined whether these variants could have an effect on (i) VEGF-induced tyrosine phosphorylation of VEGFR2, (ii) VEGF-induced HUVEC proliferation, and (iii) vitronectin-mediated cell adhesion. In addition, we determined whether there is correlation between the effects above and the ability of the variants to specifically bind recombinant human VEGFR2 and cells endogenously and over expressing the receptor.

Results

Evaluation of scVEGF as a Scaffold for Engineering New Molecular Recognition.

Our first step in evaluating the feasibility of using scVEGF as a scaffold for protein engineering was to determine its compatibility with yeast surface display. The gene for wild-type scVEGF was prepared in two parts corresponding to a fragment of VEGF chain 1 (amino acids E13 to D109) and a 14-amino acid linker SEQ ID NO:69 (GSTSGSGKS-SEGKG) followed by VEGF chain 2 (also amino acids E13 to D109). A mutant version (scVEGFmut) was prepared with four mutations corresponding to key binding residues at one pole of the molecules: chain 1 F17A, E64A; chain 2 I46A, I83A (FIG. 1A) (note that residue numbers used in this paper correspond to the residue numbers from VEGF121, not positions in scVEGF). This construct should inhibit VEGFR2 dimerization and activation by preventing a second VEGFR2 molecule from binding at the mutated face of the ligand (FIG. 2). The full genes for scVEGFwt and scVEGFmut were cloned into the yeast surface display plasmid pCT and transformed to yeast strain EBY. Yeast expressing scVEGF proteins were tested for binding to VEGFR2, demonstrating that both constructs are capable of binding the receptor, and that scVEGFwt binds with significantly higher affinity than scVEGFmut (FIG. 1B).

Figure 2:
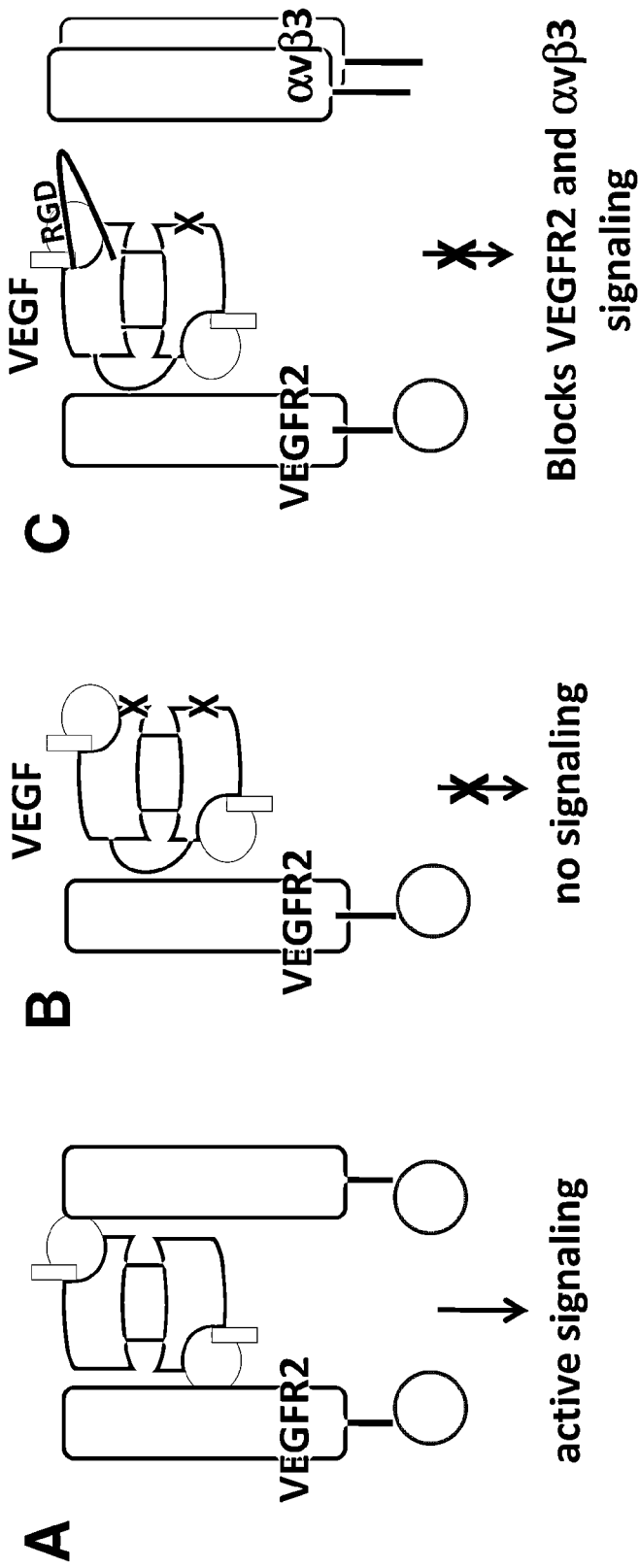
FIG. 2. Comparison of VEGF-VEGFR2 interaction with the variants proposed in this study. (A) Wild-type VEGF is a homodimer that binds to two VEGFR2 molecules to activate signaling. (B) Single-chain VEGF has one of the VEGFR2 binding sites mutated, preventing a second receptor molecule from binding and thereby antagonizing signaling. (C) The bispecific variants engineered here have one VEGFR binding site mutated with an αvβ3 integrin recognition loop, making them capable of binding VEGFR2 and/or αvβ3 integrin.
Figure 11:
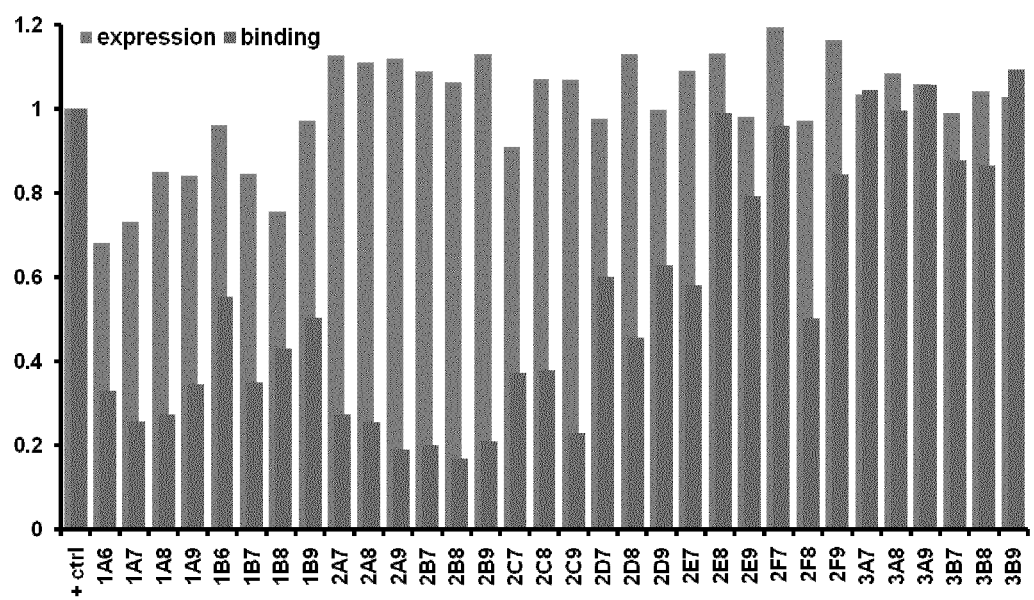
FIG. 11. Testing scVEGFmut loop libraries for protein expression and binding to VEGFR2.

To evaluate whether any of the loops on the mutated pole of scVEGF were amenable to saturation mutagenesis, we prepared libraries of three such loops, shown in FIG. 1C, in which 5-8 amino acids were removed from the loop and replaced with randomized sequences of length 6-9 amino acids. Different registers of amino acids were removed for each of the 3 loops, and each library had just a single loop replaced with a new randomized sequence. We tested each library for its tolerance to substitution by monitoring the relative expression and the relative binding to 50 nM VEGFR2 (FIG. 11). These data showed that substitution of loop 3 (FIG. 1C) residues SEQ ID NO:70 IKPHQGQ with 9 amino acids gave near wild-type binding and expression levels. Loop 1 was the least tolerant to mutagenesis while loop 2 was moderately tolerant, whereas all registers and loop lengths tested for loop 3 showed very good expression and binding levels relative to wild-type (FIG. 11).

Construction and Screening of scVEGF Libraries for Dual VEGFR2- and $\alpha_v\beta_3$ integrin-targeting.

The loop mutagenesis studies suggested that loop 3 in one chain could be replaced and engineered to bind a new target, such as $\alpha_v\beta_3$ integrin, while the overall scVEGF protein could still retain binding to VEGFR2 at the opposing face (FIG. 2C). To facilitate integrin binding, we included an RGD recognition sequence and randomized flanking residues. We made three libraries from scVEGFmut, corresponding to three positions of RGD within the loop by substituting loop 3 (IKPHQGQ) with XXRGDXXXX, XXXRGDXXX, or XXXXRGDXX, where X corresponds to any amino acid. The libraries were transformed to yeast giving 0.5-2×10$^7$ transformants per library. The yeast libraries were concurrently tested for protein expression and binding to 100 nM VEGFR2. For all three libraries, nearly the entire expressing population also bound VEGFR2, indicating that replacement of the loop again did not compromise binding to VEGFR2 at the opposite pole of the ligand.

Library Screening was Performed by Fluorescence-Activated Cell Sorting (FACS).

Figure 3:
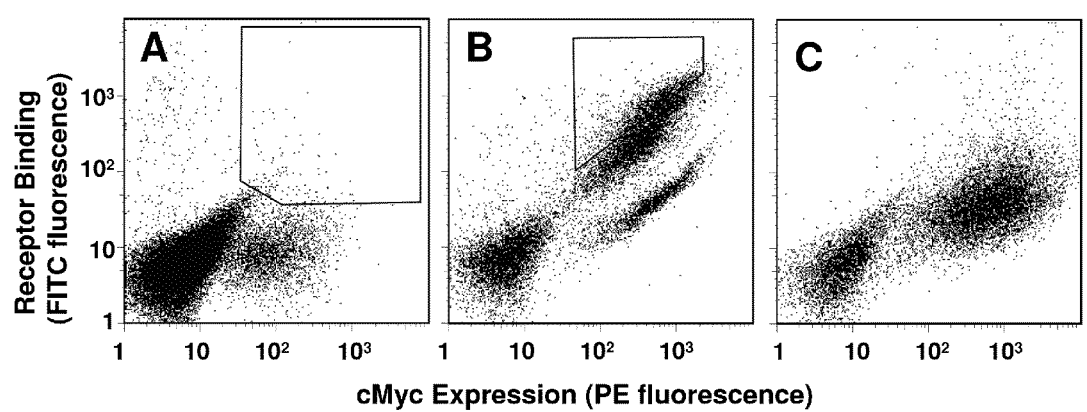
FIG. 3. FACS plots showing sorting of scVEGFrgd loop libraries. (A) Sort round 1, 250 nM $\alpha_v\beta_3$ integrin. (B) Sort round 4, 100 nM VEGFR2-Fc. (C) After sort round 7, 25 nM $\alpha_v\beta_3$ integrin.

Yeast displaying scVEGF variants were labeled with $\alpha_v\beta_3$ integrin and an anti-cMyc antibody to simultaneously monitor protein expression via a C-terminal cMyc epitope tag. After treatment with fluorescently-labeled secondary antibodies, the yeast showing the greatest receptor binding relative to expression were selected by FACS, propagated, and the process was repeated for multiple rounds. In sort round 1, the three yeast-displayed libraries were combined and a total of ~8×10$^7$ cells were screened against 250 nM $\alpha_v\beta_3$ integrin by FACS (FIG. 3A). In subsequent sort rounds, the concentration of integrin was dropped and the number of yeast sorted was in at least a 10-fold excess of the remaining library diversity. In sort round 4, the yeast were sorted against 100 nM VEGFR2 (Fc-fusion) to remove a population of proteins with weaker receptor binding (FIG. 2B). The final sort, round 7, was performed with 25 nM integrin (FIG. 3C).

Sixteen clones were sequenced after the seventh sort round and 7 unique sequences were obtained (Table 2). These bispecific clones will be referred to as the scVEGFrgd series. Surprisingly, one of the sequences had a loop that was 11 amino acids long, two residues longer than the 9-amino acid RGD loop we used for the library. The RGD consensus was found in the middle of the loop for all 7 sequences, and there was no consensus amongst the other residues save the presence of a Pro in position one for 5 out of the 7 sequences.

TABLE 2

Sequences of selected scVEGFrgd clones.
The RGD loop only is shown
(replacing residues I83-Q89 from VEGF).

| SEQ ID NO: 52, 7I | PSVRRGDSPAS |
| SEQ ID NO: 60, 7K | PTTRGDCPD |

TABLE 2-continued

Sequences of selected scVEGFrgd clones.
The RGD loop only is shown
(replacing residues I83-Q89 from VEGF).

| SEQ ID NO: 61, 7H | PGGRGDSAY |
| SEQ ID NO: 62, 7B | PHDRGDAGV |
| SEQ ID NO: 58, 7F | STDRGDASA |
| SEQ ID NO: 63, 7G | ASGRGDGGV |
| SEQ ID NO: 64, 7P | PASRGDSPP |

Affinity Maturation of scVEGF Mutants Against VEGFR2.

With scVEGF proteins capable of targeting both VEGFR2 and $\alpha_v\beta_3$ integrin prepared, we next sought to improve the affinity of these variants for VEGFR2. The mutations in scVEGFmut and scVEGFrgd clones appear to decrease their affinities for VEGFR2, presumably a result of decreased avidity and increased off-rate, due to their inability to bind to two VEGFR2 molecules. The diminished affinities of these variants for VEGFR2 relative to wild-type would presumably lead to low potency in inhibiting VEGF-mediated processes, which was observed in the previous study on single-chain VEGF variants. Therefore, improvement of VEGFR2 affinities is a critical step in preparing efficacious antagonists.

Our strategy to affinity mature the scVEGF variants against VEGFR2 involved screening random mutagenesis libraries against VEGFR2 and isolating the mutants with highest affinity in increasingly stringent sorts. However, during this process it was critical that the isolated variants did not recover the second VEGFR2 binding site (i.e. change the mutated residues back to wild-type amino acids or acquire compensatory mutations), as the resulting proteins would presumably be agonists of the receptor. Since we could not control for reversion mutations in our error-prone mutagenesis, we adopted a strategy involving screening two libraries starting from two different scVEGF variants: scVEGFmut and scVEGFrgd-7B. Since the primary VEGFR2 binding loop in scVEGFrgd-7B was substituted, it would be highly unlikely that variants that recovered binding to VEGFR2 at this site would be isolated. Thus, if variants with compensatory mutations were isolated from the scVEGFmut library, mutations that improve affinity at the proper VEGFR2-binding pole could still be identified by comparison to mutations selected in the scVEGFrgd-7B library. In addition, if similar mutations were identified from both libraries, it would serve as confirmation that those mutations were involved in improving VEGFR2 affinity.

Figure 4:
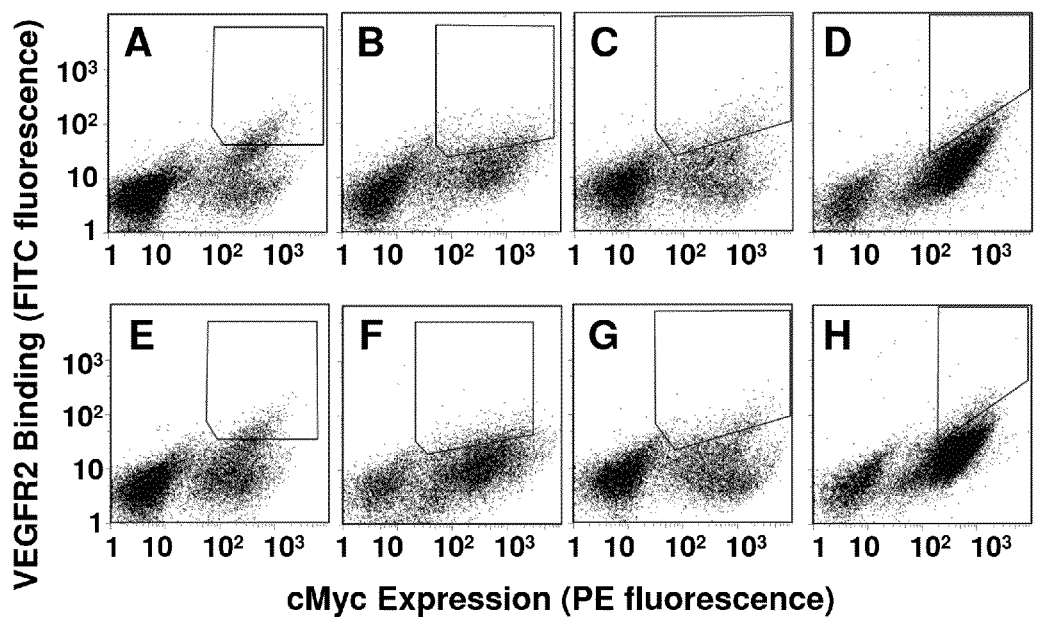
FIG. 4. FACS plots showing sorting of scVEGFmut (A-D) and scVEGFrgd-7B (E-H) error-prone mutagenesis libraries.

We prepared libraries from scVEGFmut and scVEGFrgd-7B by error-prone PCR using nucleotide analogs and varying the mutation frequency from ~0.2% to ~2%. The libraries were sorted by FACS over 6 rounds using increasing stringency (lower concentrations of VEGFR2 extracellular domain). The total DNA from sort rounds 5 and 6 was subjected to and additional round of mutagenesis, then subjected to 6 rounds of FACS (FIG. 4). The final sort round for these libraries was performed against 200 pM VEGFR2, a concentration at which yeast-displayed scVEGFmut and scVEGFwt did not appreciably bound to the receptor. Sequencing of 14 clones selected from the final sorting round for the scVEGFmut and scVEGFrgd-7B libraries yielded 9 and 8 unique sequences, respectively. Protein sequences are provided in the SEQLIST.

Figure 5:
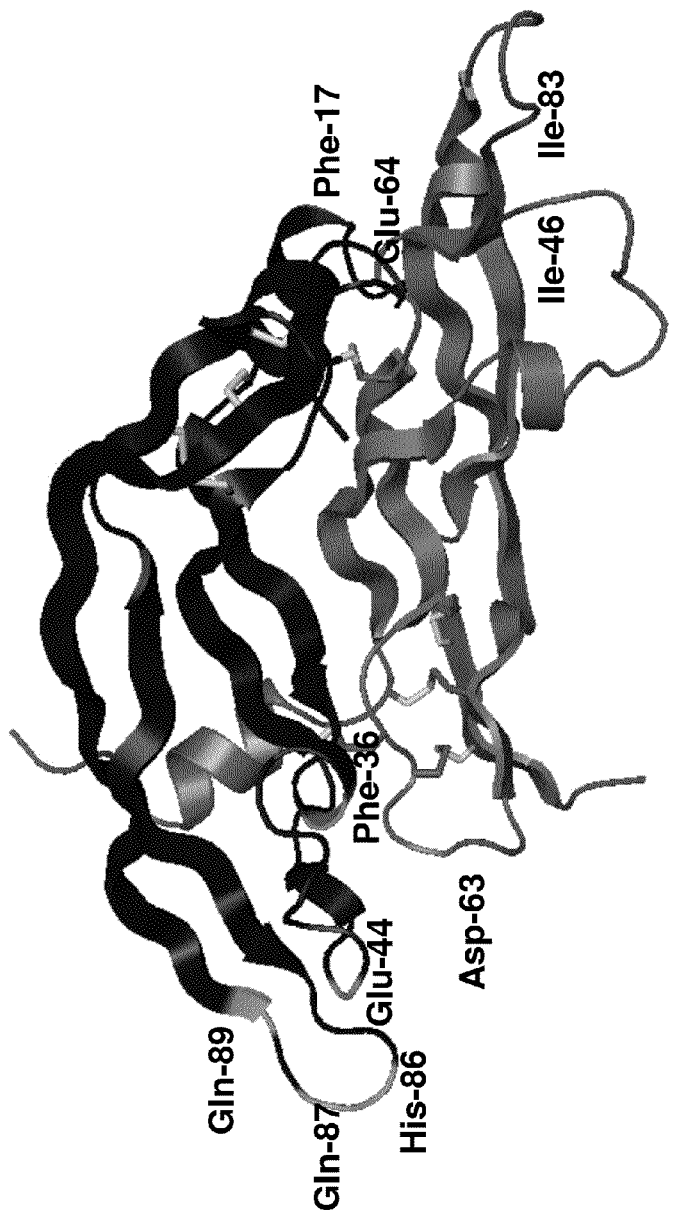
FIG. 5. VEGF structure showing positions of the most common mutations selected from the scVEGF affinity maturation libraries. Chains 1 and 2 are shown in dark and light blue, respectively. Mutations in scVEGFmut geared toward disrupting binding at one pole of the protein are shown in red. Mutations commonly appearing in the affinity matured clones are shown in green.
Figure 12:
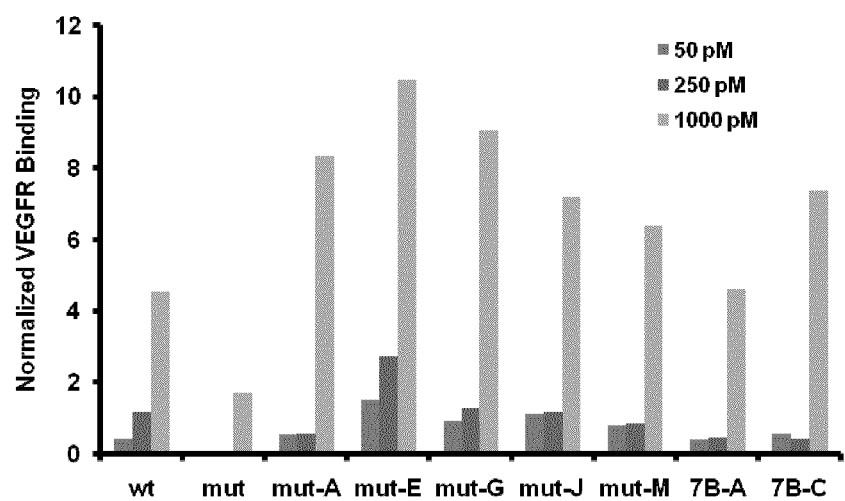
FIG. 12. Testing scVEGFmut and scVEGFrgd-7B affinity matured clones for binding to VEFGR2.

Most of the most common mutations, chain 1 F36L, E44G, H86Y, Q87R, Q89H, and chain 2 D63N/H are located in the correct binding interface for the pole of scVEGFmut that can bind to VEGFR2 (H86Y, Q87R, and Q89H are in the main recognition loop) (FIG. 5). Some of the other mutations observed, such as chain 2 R82G and I91T, may contribute to reversion of binding at the opposite pole, though none of the mutations appeared in more than one clone from both libraries. Thus these mutations are likely to be incidental or backbone mutations that have little effect on VEGFR2 binding. All of the individual clones from the scVEGFmut and scVEGFrgd-7B libraries (Table 3) tested for binding to VEGFR2 showed improved binding for the receptor relative to scVEGFmut and scVEGFwt (FIG. 12).

TABLE 3

Clones from scVEGF affinity maturation libraries.
Mutations listed refer to positions in VEGF121 and are in addition to the specific mutations that block binding at one pole (chain 1 F17A, E64A; chain 2 I46A, I83A) or substitution with the RGD loop for the scVEGFrgd-7B clones.

| Clone | Chain 1 mutations | Chain 2 mutations |
|---|---|---|
| scVEGFmut-A | V15A, R23K, F36L, E44G, H86Y | E42K, M81T |
| scVEGFmut-E | F36L, E44G, D63G, Q87R | K16R |
| scVEGFmut-J | M18R, F36L, H86Y, Q89H | I91T |
| scVEGFmut-M | Q22R, L32S, F47L, I76T, H86Y, Q87R | P53S, M78V, R82G |
| scVEGFrgd-7B-A | F36L, H86Y, Q87R, D63N | K107R |
| scVEGFrgd-7B-C | R23G, F36L, H86Y, D109G | Q79R, K108R |
| scVEGFrgd-7B-K | F36L, H86Y | K16R, K108E |

Recombinant Production of Soluble scVEGF in *P. pastoris*.

The genes for scVEGFwt, scVEGFmut, scVEGFrgd clones 7B, 7H, 7I, and 7P, as well as affinity matured scVEGFmut clones mA, mE, mJ, and mM were cloned into the pPIC9K vector for expression in *P. pastoris* strain GS115. The proteins were expressed with a C-terminal hexahistidine tag, and either with or without an N-terminal FLAG epitope tag (the untagged version is shown in the sequence listing). We originally prepared the proteins only with the His tag, but we discovered this tag could not be effectively used in cell binding assays, so we made future protein preparations that also included the N-terminal FLAG tag, which proved more effective for monitoring cell binding. The crude *P. pastoris* supernatants were purified by Ni-NTA beads. A reduced gel of the resulting proteins showed 3 bands, presumably resulting from 3 different glycosylation states and consistent with the presence of 2 N-linked yeast glycosylation sites. In addition, a non-reduced gel of the resulting proteins revealed the presence of a mix of disulfide-linked multimers. To complete purification, the proteins were first treated with endoHf to cleave glycosylation and were then subjected to gel filtration FPLC to remove the endoHf and multimeric proteins. The fully purified protein as a single peak in analytical gel filtration FPLC and did not revert to multimers. MALDI mass spectrometry revealed a broad range of peaks several hundred Daltons larger than the expected mass and varying by several hundred Daltons, presumably due to small variation in cleavage of glycans.

Binding Kinetics of scVEGF Variants to VEGFR2 Using BIAcore.

Figure 6:
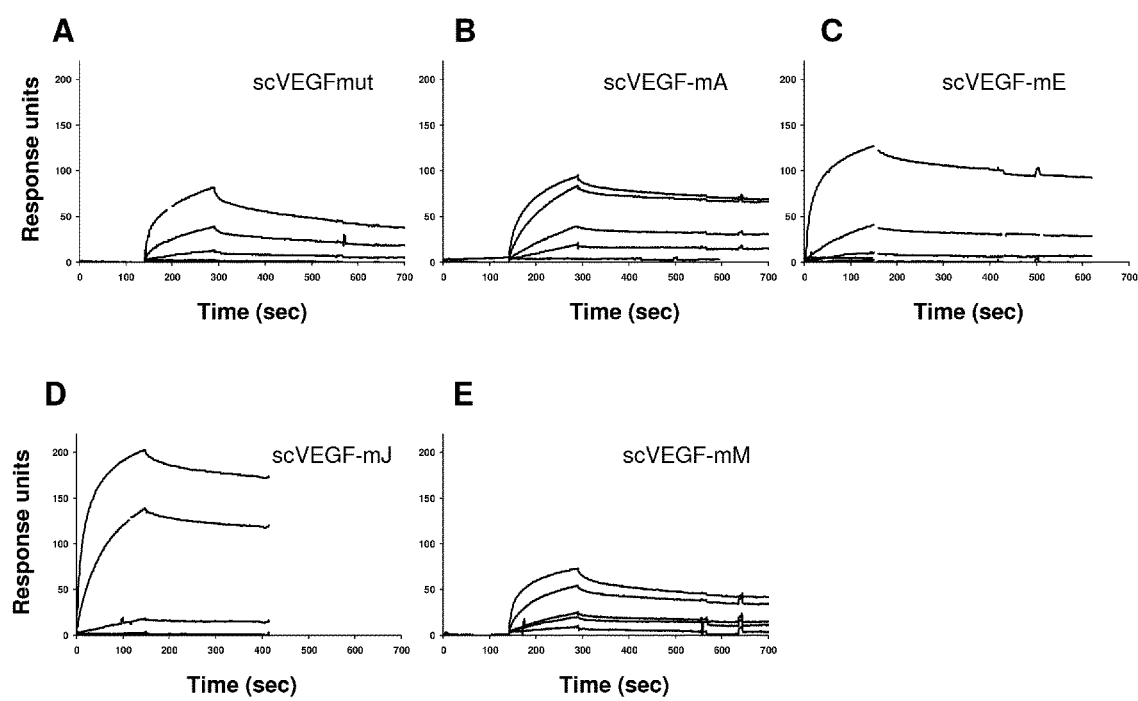
FIG. 6. SPR interaction analysis of scVEGF variants with VEGFR2. Representative tracing of association and dissociation of different concentrations of scVEGF variants, during perfusion at 30 µl/min over VEGFR-2 immobilized to CM-5 sensor chip.

SPR analyses confirmed that all the soluble scVEGF variants injected at increasing concentrations specifically interacted with the recombinant human VEGFR-2 immobilized onto the sensor chip (FIG. 6). Non-specific binding was estimated by applying bovine serum albumin (BSA). The best fit was obtained using a 1:1 binding model considering all proteins as monomeric. The affinity constants ($K_D$) as well as the kinetic parameters ($k_{on}$ and $k_{off}$) are shown in Table 4. All the affinity matured proteins bound VEGFR2 better than scVEGFmut (~2 nM vs. ~20 nM $K_D$ values). The complex dissociation ($k_{off}$) was slower for scVEGFwt, scVEGF-mA, mE and mJ (~3-7×10$^{-4}$ 1/sec) than for scVEGFmut and scVEGF-mM (~1×10$^5$ 1/sec). Higher $k_{on}$ values were observed for both the affinity matured proteins and scVEGFwt (~2×10$^5$ 1/M×sec) as compared to scVEGFmut (~8×10$^4$ 1/sec). It is worth noting that the regeneration of VEGFR2 immobilized on the sensor chip could be achieved by perfusing 3M $MgCl_2$ in the case of scVEGFwt, scVEGFmut, scVEGF-mE, mM but not for scVEGF-mA and mJ, where 3M $MgCl_2$ with 10 mM NaOH was needed which might indicate different binding interactions.

TABLE 4

Binding kinetics of the scVEGF variants to immobilized VEGFR-2$^a$.

| Protein | $K_D$ (nM) | $K_{on}$ (1/M × s) | $K_{off}$ (1/s) |
|---|---|---|---|
| scVEGFwt | 4 ± 2 | (2 ± 1) × 10$^5$ | (7 ± 2) × 10$^{-4}$ |
| scVEGFmut | 18 ± 1 | (8.3 ± 0.5) ) × 10$^4$ | (1.46 ± 0.05) × 10$^{-3}$ |
| scVEGF-mA | 2.1 ± 0.4 | (2.4 ± 0.8) ) × 10$^5$ | (4.9 ± 0.9) × 10$^{-4}$ |
| scVEGF-mE | 2.8 ± 0.5 | (2.2 ± 0.4) ) × 10$^5$ | (6.1 ± 0.4) × 10$^{-4}$ |
| scVEGF-mJ | 1.6 ± 0.5 | (2 ± 1) ) × 10$^5$ | (3 ± 2) × 10$^{-4}$ |
| scVEGF-mM | 3.8 ± 0.8 | (2.9 ± 0.6) ) × 10$^5$ | (1.08 ± 0.07) × 10$^{-3}$ |

$^a$All of the numbers are determined by BIAcore analysis and represent the mean ± S.E. from at least three separate determinations.

Affinities of Soluble scVEGF Variants Determined by Cell Binding.

Figure 7:
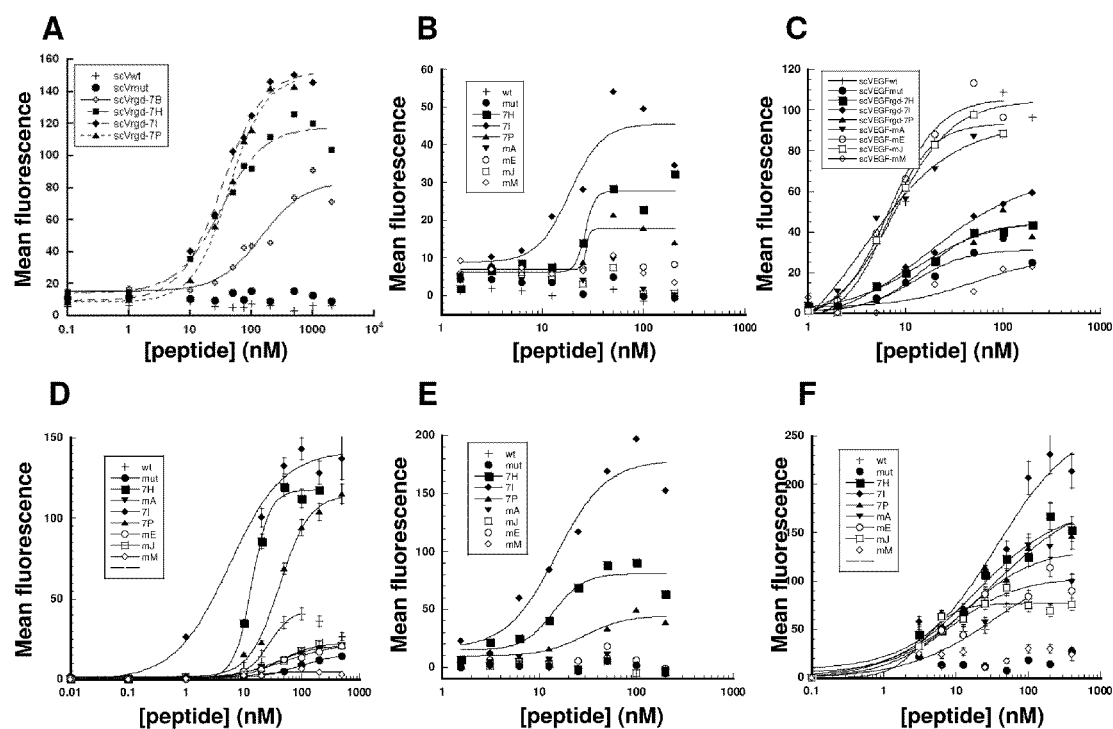
FIG. 7. Binding titrations against cell lines. (A) K562$\alpha_v\beta_3$ cells. (B) PAE cells (C) PAE-KDR cells (also express porcine $\alpha_v\beta_3$). (D) HUVEC cells (E) U87MG cells (F) SVR cells.

We tested the recombinant proteins for their ability to bind integrins and VEGFR2 on the surface of several cell types. We initially tested the scVEGFrgd analogs and affinity-matured scVEGF mutants, as well as scVEGFwt and scVEGFmut for binding to a K562 cell line that stably expresses $\alpha_v\beta_3$ receptors and do not express VEGFR2. As expected, scVEGFwt, scVEGFmut and the affinity-matured scVEGF mutants did not bind these cells, but the scVEGFrgd clones did. Clones 7H, 7I, and 7P bound with $K_D$ values ~35 nM, while 7B had a substantially worse $K_D$ of 143 nM (FIG. 7A and Table 4). Among the scVEGFrgd protein variants, only 7H, 7I, and 7P were used in subsequent studies. Both the affinity-matured scVEGF and the scVEGFrgd proteins did not bind to wild-type K562 cells, which express $\alpha5\beta1$, and to K562 cells transfected with $\alpha v\beta5$ or $\alpha iib\beta3$ integrins indicating the specificity of the scVEGFrgd proteins to $\alpha_v\beta_3$ receptors.

We next tested the binding of scVEGF variants against PAE cells (FIG. 7B and Table 5). PAE cells are a porcine aortic endothelial cell line that endogenously expresses porcine $\alpha_v\beta_3$ integrin. We found that the scVEGFrgd proteins, but not scVEGFwt, scVEGFmut or the affinity-matured scVEGF proteins, bound with $K_D$ values ~25 nM to these cells. Next, we tested the proteins against a PAE cell line that has been stably transfected to express human VEGFR2 (PAE/KDR, FIG. 7C and Table 5). scVEGFwt bound with a $K_D$ of 10 nM, while scVEGFmut and the scVEGFrgd clones 7H, 7I, and 7P bound with $K_D$'s of 16-21 nM. Since binding of these clones to PAE/KDR cells is dependent on binding to VEGFR2, it is unsurprising that scVEGFmut and the RGD-containing clones all bind with the same affinities and slightly less than the scVEGFwt. Importantly, the affinity-matured scVEGF mutants scVEGF-mA, -mE, and -mJ bound with single-digit nM affinities (similar to scVEGFwt), while scVEGF-mM had slightly worse binding than scVEGFmut at 34 nM. The maximum binding levels were substantially higher for the highest affinity clones scVEGF-mA, -mE, and -mJ. This could be due to much slower $k_{off}$ rates for these clones (as discussed above in the Biacore data section).

TABLE 5

Summary of cell binding data for scVEGF variants. $K_D$ values are expressed in nM.

| Protein | K562$\alpha_v\beta_3$ | PAE | PAE-KDR | HUVEC | U87MG | SVR |
|---|---|---|---|---|---|---|
| scVEGFwt | a | a | 9.8 | 28 ± 4 | a | 32 ± 5 |
| scVEGFmut | a | a | 17 ± 8 | 101 ± 7 | a | a |
| scVEGFrgd-7B | 140 ± 10 | b | b | b | b | b |
| scVEGFrgd-7H | 36 ± 12 | 26.5 | 16 ± 8 | 12 ± 4 | 15.6 | 18 ± 4 |
| scVEGFrgd-7I | 34 ± 2 | 18.6 | 20 ± 11 | 6 ± 3 | 13.9 | 37 ± 5 |
| scVEGFrgd-7P | 37 ± 6 | 26.9 | 21 ± 10 | 45 ± 5 | 29 | 31 ± 5 |
| scVEGF-mA | a | a | 5.7 ± 0.5 | 36 ± 5 | a | 13 ± 3 |
| scVEGF-mE | a | a | 6.6 ± 1.8 | 53 ± 6 | a | 8 ± 4 |
| scVEGF-mJ | a | a | 6.9 ± 1.5 | 39 ± 6 | a | 3 ± 1 |
| scVEGF-mM | a | a | 34 ± 18 | a | a | a | a No binding was observed at the highest concentration tested (1 µM)
b Not tested All proteins, except scVEGFmut and scVEGF-mM, bound human umbilicial vein endothelial cells (HUVEC; which express both VEGFR2 and $\alpha_v\beta_3$ integrin), with $K_D$s below 100 nM (FIG. 7D and Table 5). The scVEGFrgd proteins 7H and 7I, showed the highest affinity (12 nM and 6 nM, respectively), which was stronger than for the scVEGFwt, in agreement with their ability to bind both receptors endogenously expressed on these cells. The affinity-matured scVEGF proteins bound with a $K_D$ of ~40 nM which is stronger than the binding of the scVEGFmut.

Like in HUVEC, all proteins except scVEGFmut and scVEGF-mM, bound SVR angiosarcoma cells with $K_D$s below 40 nM (FIG. 7F and Table 5). However, the affinity-matured scVEGF mutants ($K_D$'s of 8 nM) bound better than the scVEGFrgd proteins ($K_D$'s of 30 nM). Both HUVEC and SVR cells express VEGFR2 and $\alpha_v\beta_3$ integrin, except that SVR are murine cell lines.

As shown in FIG. 7E, all proteins bound U87MG human glioblastoma cells similar to PAE cells; scVEGFrgd proteins, but not scVEGFwt, scVEGFmut or the affinity-matured scVEGF proteins, bound with $K_D$ values ~20 nM to these cells. This is probably because the U87MG cell lines, similar to PAE cells, do not express VEGFR2 (confirmed by flow cytometry experiments).

It is also worth noting that binding for all concentrations of the scVEGF proteins was performed in non-ligand-depleting conditions, so the affinities are the same as what is reported here.

Inhibition of VEGF-Mediated VEGFR-2 Autophosphorylation in Endothelial Cells.

Figure 8:
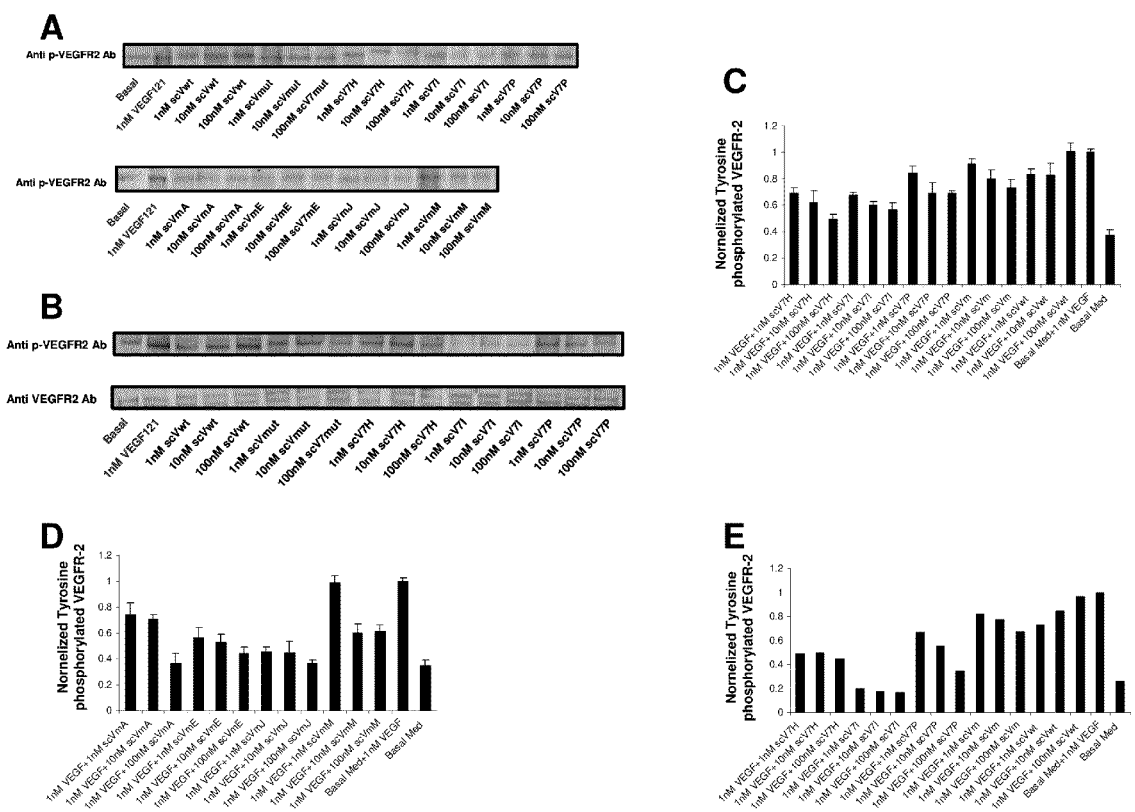
FIG. 8. Effect of scVEGF variants on VEGF-stimulated tyrosine phosphorylation of VEGFR2 in HUVEC in the absence (A) or presence (B) of vitronectin. Results from vitronectin-free (C-D) and experiments including vitronectin (E) were analyzed by densitometry on chemidoc and values are means of three independent experiments. Bars, ±SD.

The scVEGF variants were tested for their ability to inhibit VEGF-induced autophosphorylation of VEGFR-2 in HUVEC in the presence or absence of adhesive vitronectin (FIG. 8). When coated on surfaces, very low concentrations of vitronectin promote endothelial cell attachment and induce spreading and migration of cells. While in the absence of vitronectin, the bispecific scVEGFrgd variants were only slightly more potent than the scVEGFmut (~20% inhibition) (FIGS. 8A and C), in the presence of vitronectin they were significantly more potent with scVEGFrgd-7I being the most active (80% inhibition) (FIGS. 8B and E). This difference is due to the ability of the bispecific variants, but not the scVEGFmut, to block both the binding of vitronectin and VEGF to $\alpha V\beta 3$ integrin and VEGFR2, respectively. Because of their specificity to only VEGFR2, the ability of the affinity matured variants to inhibit VEGF-induced VEGFR2 autophosphorylation in HUVEC cells was tested only in the absence of vitronectin. The ability was highly correlated with the affinity of the proteins to the immobilized VEGFR2 (BIAcore data) and to HUVEC cells. The variants with high affinity (scVEGF-mA,mE and mJ) demonstrated a strong inhibition activity, whereas the variants with lower affinity (scVEGFmut and scVEGFmM) were less active (FIGS. 8C and D). Not surprisingly, scVEGFwt did not inhibit VEGFR2 phosphorylation, and in fact it was able to promote phosphorylation when added at the highest concentration.

Inhibition of VEGF-Mediated Proliferation of Endothelial Cells.

VEGF induced signal transduction for the proliferation of endothelial cells is mainly mediated by VEGFR2. Therefore, we next wanted to evaluate the relationship of the abilities of the scVEGF variants to inhibit VEGF-mediated VEGFR2 autophosphorylation and endothelial cells proliferation. The effects of the scVEGF variants on endothelial proliferation were assessed in HUVEC cells stimulated with VEGF, in the presence or absence of vitronectin, using the DNA synthesis rate as a measure of cell proliferation. All the proteins inhibited the proliferation of HUVECs in a dose-dependent manner.

Figure 9:
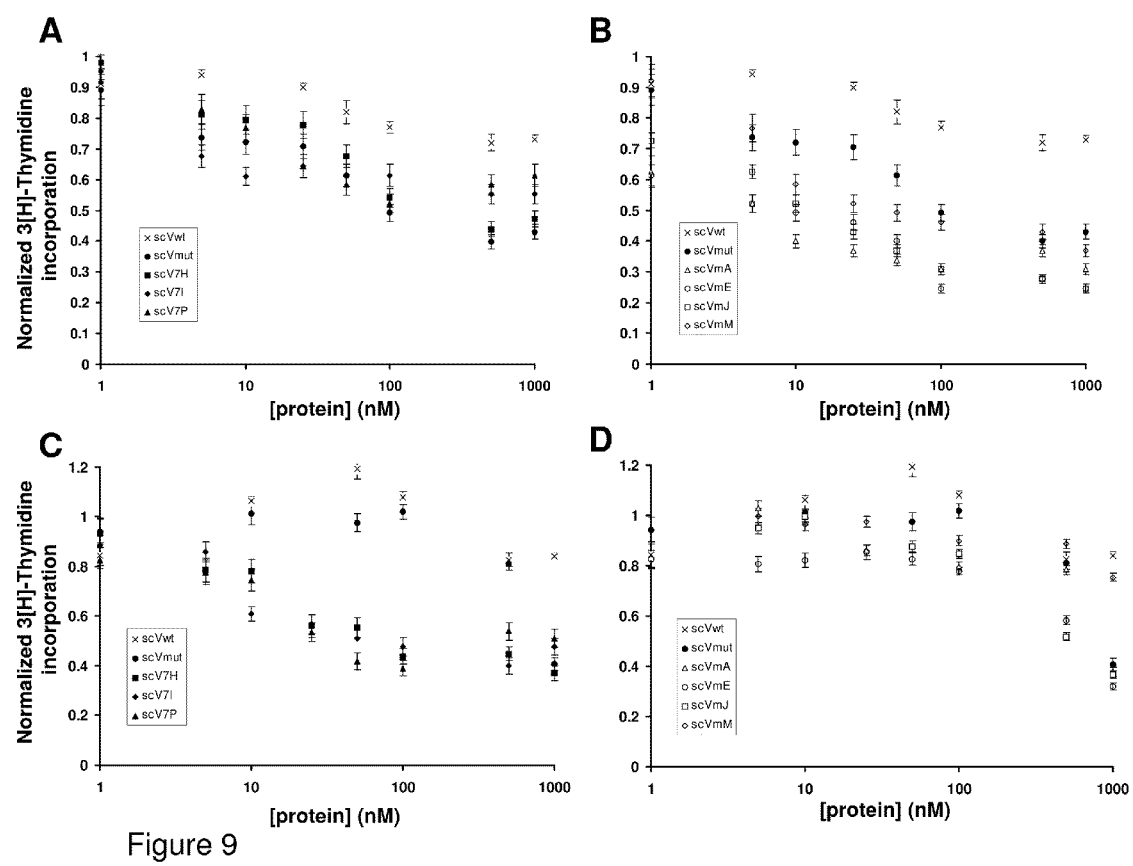
FIG. 9. Effect of scVEGF variants on VEGF-stimulated HUVEC proliferation in the absence (A-B) or presence (C-D) of vitronectin. Values expressed as means of three independent experiments. Bars, ±SD.

As expected, in the absence of vitronectin, the bispecific scVEGFrgd variants were as active as the scVEGFmut in inhibiting proliferation showing the highest activity between 50-100 nM (FIG. 9A). In contrast, in the presence of vitronectin the bispecific variants were much more active (FIG. 9C). The ability of the affinity matured variants to inhibit VEGF-induced HUVEC proliferation was highly correlated with the affinity of the proteins to the immobilized VEGFR2 receptor (BIAcore data) and to HUVEC cells. The variants with high affinity (scVEGF-mA,mE and mJ) demonstrated a strong inhibition activity, whereas the variants with lower affinity (scVEGFmut and scVEGFmM) were less active (FIGS. 9B and D).

Bispecific variants with high affinity for both $\alpha V\beta 3$ integrin and VEGFR2 could significantly inhibit HUVEC proliferation in the presence of vitronectin (FIG. 9C), whereas the affinity matured mutants with high affinity only to VEGFR2 facilitated strong inhibition of proliferation in the absence of vitronectin and weak inhibition in the presence of vitronectin (FIGS. 9B and D, respectively). These results suggest that the affinity strength of the scVEGF variants mostly correlates with their ability to inhibit VEGF-mediated proliferation of HUVEC. As in the phosphorylation assay, scVEGFwt did not inhibit HUVEC proliferation, and in the presence of vitronectin it was actually able to promote proliferation when added at 10-100 nM.

Inhibition of Vitronectin-Mediated Cell Adhesion by scVEGF Variants.

Figure 10:
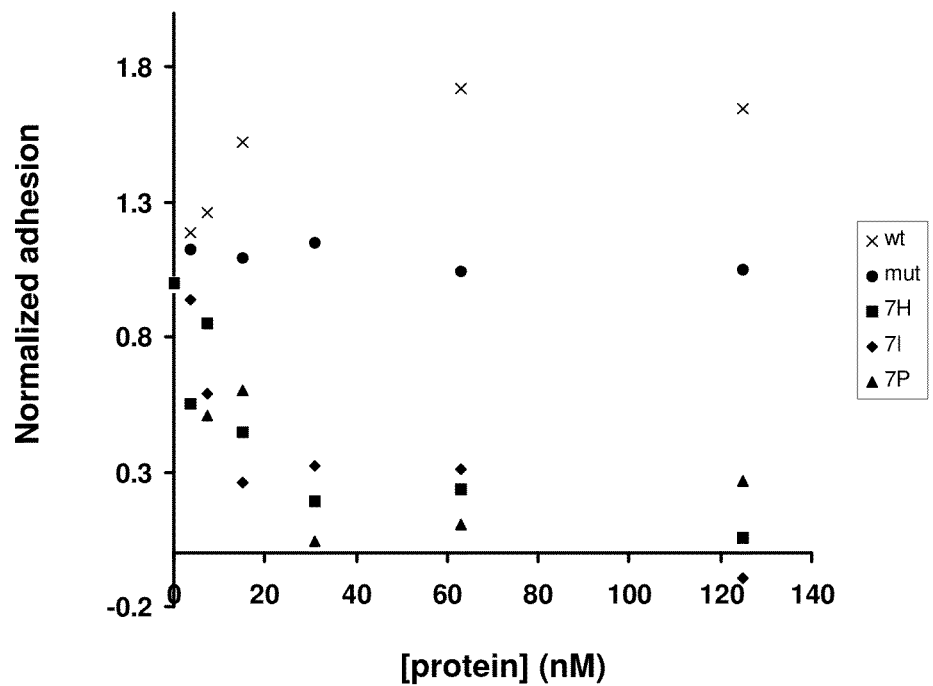
FIG. 10. Inhibition of vitronectin-mediated HUVEC adhesion by engineered scVEGF variants. Vitronectin-coated wells were incubated with cells for 2 h with the indicated concentrations of scVEGF variants. Adherent cells remaining after several wash steps were quantified by crystal violet staining and determining the absorbance at 600 nm. Values were background subtracted using a negative control containing no peptide. Symbols scVEGF variants (x) scVEGFwt; (■) scVEGF-7H; (♦) scVEGF-7I; (●) scVEGFmut; (Δ)scVEGF-7P.

We next tested whether the engineered scVEGF variants could inhibit cell adhesion mediated by vitronectin, the primary ligand for αvβ3 integrin. We incubated HUVEC cells with varying concentrations of proteins in 96-well plate pre-coated with vitronectin to determine the ability of the proteins to inhibit cell adhesion. The bispecific scVEGFrgd variants were able to block vitronectin-mediated adhesion of the HUVEC cells with $IC_{50}$ values <10 nM (FIG. 10). The $IC_{50}$ values for inhibition of cell adhesion by the scVEGFmut could not be determined since there was no inhibition at the concentrations tested. scVEGFwt was able to stimulate cell adhesion to vitronectin with saturation at 60 nM.

Materials and Methods

Preparation of scVEGF Constructs and Libraries.

The scVEGF constructs were prepared by PCR assembly using overlapping primers to prepare two inserts for chain 1 and a 14-amino acid linker/chain 2. Amplification was performed using end primers with NheI and BamHI restriction sites for chain 1 and BamHI and MluI restriction sites for the 14-amino acid linker/chain 2. The two inserts, followed by a cMyc epitope tag and stop codons flanked by a XhoI restriction site were cloned into the pCT yeast display vector using a multi-step cloning procedure.

Libraries were prepared starting with the scVEGFmut construct. Full genes with appropriate loops replaced with NNS degenerate codons were prepared for replacement of chain 1 (loop 1) or chain 2 (loops 2 and 3). pCT vector digested with NheI/BamHI (loop 1) or BamHI/MluI (loops 2 and 3) was co-electroporated with each insert into freshly prepared electrocompetant yeast strain EBY100. The yeast were allowed to recover for 1 h in YPD at 30° C. then were transferred to selective SD-CAA media. Libraries containing the RGD sequence and randomized flanking residues in loop 3 were prepared analogously.

Random mutagenesis libraries were prepared from scVEGFmut using error-prone PCR as described. Briefly, PCR was performed in the presence of nucleotide analogs dPTP and 8-oxo-dGTP, using primers flanking the gene. The concentration of nucleotide analogs and number of cycles was varied in order to give a range of mutation frequencies of ~0.2-2%. The resulting inserts were amplified and transformed into yeast with digested plasmid as described above. After 6 rounds of sorting, library plasmid DNA was extracted from yeast using a ZymoPrep kit (Zymo Research) and subjected to error-prone PCR as described above. The second generation library was similarly transformed to yeast and sorted as described below. For all libraries, transformation frequency was estimated by dilution plating on selective SD-CAA plates. Typical library sizes were $0.5-2\times10^7$ transformants. For sequencing of individual clones, plasmid DNA prepared by ZymoPrep was transformed to E. coli XL-1 Blue (Strategene) and individual colonies were submitted for sequencing (MCLabs, S. San Francisco, Calif.).

Sorting RGD Loop Libraries.

Yeast displayed libraries were induced for expression in SG-CAA media. Approximately $5-20\times10^6$ yeast were labeled with $\alpha_v\beta_3$ integrin (R&D systems, octyl-glucopyranoside formulation) and a 1:200 dilution of chicken anti-cMyc antibody (Invitrogen) in integrin binding buffer (IBB, 20 mM Tris pH 7.5, 100 mM NaCl, 1 mM $MgCl_2$, 1 mM $MnCl_2$, 2 mM $CaCl_2$, and 1 mg/mL BSA) for 2 h at room temperature. The cells were spun down, aspirated, and resuspended in ice-cold BPBS (PBS+1 mg/mL BSA) containing a 1:25 dilution of fluorescein-labeled mouse anti-$\alpha_v\beta_3$ (BioLegend) and a 1:100 dilution of phycoerythrin-conjugated anti-chicken-IgY (Santa Cruz Biotechnology). After 20 min on ice, the yeast were pelleted and the supernatant was removed. One intermediate sort was performed against VEGFR2-Fc; in this case a fluorescein mouse anti-Fc antibody (Sigma) was used for detection of receptor binding. The yeast were then sorted using a Vantage SE/DiVa Vantoo instrument (Stanford FACS Core Facility) and CellQuest software. In each sort ~1-2% of yeast were collected, and in subsequent sorts at least 10-fold more yeast were sorted than collected in the previous round. Concentrations of receptor used in each sort round were as follows: sort 1—200 nM $\alpha_v\beta_3$, sort 2—100 nM $\alpha_v\beta_3$, sort 3—100 nM $\alpha_v\beta_3$, sort 4—100 nM VEGFR2-Fc, sort 5—50 nM $\alpha_v\beta_3$, sort 6—50 nM $\alpha_v\beta_3$, sort 7—25 nM $\alpha_v\beta_3$.

Sorting scVEGFmut Affinity Maturation Libraries.

Yeast displayed libraries were sorted as described above using VEGFR2 extracellular domain (Calbiochem) and a fluorescein-conjugated anti-VEGFR2 antibody (R&D Systems). Concentrations of receptor used in each sort round were as follows: mutagenesis round 1, sort 1—100 nM, sort 2—50 nM, sort 4—25 nM, sort 5—5 nM, sort 6—2 nM, mutagenesis round 2, sort 1—25 nM, sort 2—5 nM, sort 3—2 nM, sort 4—1 nM, sort 5—500 pM, sort 6—200 pM.

Production and Purification of Proteins from P. pastoris.

Protein production was performed using the P. pastoris expression kit (Invitrogen). Genes for protein production were cloned between the AvrII and MluI restriction sites in the Pichia expression plasmid pPIC9K with (or without) an N-terminal FLAG tag between the SnaBI and AvrII restriction sites and a C-terminal hexahistidine tag between the MluI and NotI restriction sites. Plasmid (5-10 μg) was linearized by digestion with SacI and electroporated into freshly prepared electrocompetent P. pastoris strain GS115. The yeast were then plated on RDB plates for recovery, and then transferred to YPD plates containing 4 mg/mL geneticin for selection of multiple transformants. Individual colonies were selected and grown in BMGY cultures overnight then transferred to BMMY to induce protein production. The BMMY cultures were maintained with ~0.5% methanol over 3 days then tested for expression using Western Blot against their FLAG (or His) tag.

scVEGF Affinity Determination by BIAcore Analysis.

Binding of scVEGF proteins (incrementing concentrations from 0.2 nM to 200 nM) to immobilized human VEGFR2 (>90% SDS PAGE purity, Calbiochem) was done via surface plasmon resonance (SPR), using a BIAcore 3000 system (BIAcore, Inc., Uppsala, Sweden) as previously described with modifications. The purified VEGFR2 (40 μg/ml in 10 mM sodium acetate, pH 5.5) was covalently attached via amine coupling to sensor chip CMS, according to the instructions of the manufacturer, to 2300-2700 resonance units (RU). Bound ligand was then perfused in IBB/BSA/ 0.005% surfactant P20, pH 7.4 at 25° C. at a flow rate of 30 μl/min. The specificity of analyte binding was analyzed by correction for non-specific binding, via perfusion of non-coupled control channels. Association ($k_{on}$) and dissociation ($k_{off}$) rate constants were calculated via curve fitting, using the BIAevaluation 2.0 software, assuming a 1:1 model, considering all proteins as monomeric at concentrations tested. The affinity constant ($K_D$) was calculated from the ratio of dissociation rate ($k_{off}$)/association rate ($k_{on}$). The rapid increase and decrease in resonance signal, preceding association and dissociation respectively (buffer jumps), were excluded from evaluation. The chip was regenerated by injection of 3M $MgCl_2$ with 10 mM NaOH for 30 s at 30 μl/min.

Cell Binding Assays.

Wild-type K562 cells were maintained in IMDM media (Gibco) supplemented with 10% FBS. Media for K562 cells expressing integrins also had 1.2 mg/mL geneticin. Cells were maintained in suspension at concentrations of ~2-20× $10^5$ cells/mL. PAE and PAE/KDR cells were grown in F-12 (Ham's) Nutrient Media (Gibco) with 10% FBS and 1% Pen/strep. HUVEC cells were grown in full EGM-2 media (Lonza) containing 2% FBS and growth factor supplements. U87MG cells were grown in DMEM (high glucose) media (Gibco) containing 10% FBS and 1% Pen/strep. SVR cells were grown in DMEM media containing 10% FBS and 1% Pen/strep. Cells grown on plates were split at 80-90% confluence using 0.05% trypsin-EDTA.

For cell binding assays, $10^5$ cells were used per condition. Cells were suspended in IBB (0.1-1 mL volume) and protein was added as a 10× or 100× stock in an amounts that were sufficient to avoid ligand depletion at all ligand concentrations tested. The cells were incubated at 4° C. with gentle agitation to prevent settling for 4-6 h, then spun down at 1000 rpm (0.1 rcf) at 4° C. for 3 min and the supernatant was aspirated. The cells were then resuspended in 20 µL BPBS containing a 1:40 dilution of fluorescein-conjugated anti-His antibody (for K562 cells) or a 1:100 dilution of phycoerythrin-conjugated anti-FLAG antibody (for the other cells). After 20 minutes, the cells were resuspended in 1 ml BPBS, centrifuged and the supernatant was aspirated. The cells were kept as pellets on ice until analysis by flow cytometry. Mean fluorescence for each concentration was calculated using FlowJo (Treestar, Inc) then plotted versus log concentration, and the data were fit to a sigmoidal curve to calculate dissociation constants using Kaleidograph (Synergy Software).

VEGFR-2 Autophosphorylation Assay.

VEGFR-2 phosphorylation assay was carried out following the procedure previously described with small modifications. Briefly, subconfluent HUVECs were grown in growth factor and serum-depleted EBM-2 medium for 20 h prior to experimentation. After pretreatment with 1 mM sodium orthovanadate ($Na_3VO_4$) for 20 min, the cells were incubated in the presence of 1 nM of VEGF121 and different concentrations of the protein variants for 10 min at 37° C. The cells were then washed in phosphate-buffered saline (PBS) with 1 mM $Na_3VO_4$ and lysed in ice-cold 1% Triton X-100 lysis buffer for 2 h (20 mM Tris pH 7.4, 150 mM NaCl, 1% TritonX-100, 1×APC, 1×AEBSF, 1 mM $Na_3VO_4$, 1× complete protease inhibitor tablet). The lysates were clarified by centrifugation (13,000 rpm for 10 min at 4° C.). Protein concentrations were measured using a Bio-Rad protein assay and the same amounts of protein of each sample were used for analysis. Cell lysates were subjected to 4-12% SDS-PAGE and transferred to a nitrocellulose sheet. The blots were incubated with a blocking solution (5% milk containing TBST washing buffer (20 mm Tris-HCl, pH 7.4, 150 mm NaCl, 0.3% Tween 20)) and probed with primary antibodies (Y951 or VEGFR2) diluted in blocking solution for overnight at 4° C. The signals were visualized using HRP-conjugated anti rabbit secondary antibodies and exchanged chemiluminescence (ECL plus, Amersham) according to the manufacturer's instructions. The immunoreactive bands were quantified on a chemidoc system. Blots were stripped and re-probed to determine total amounts of VEGFR2 present. Unstimulated (basal) and VEGF121-stimulated cells were used as negative and positive controls, respectively. The above assay was also done in the presence of vitronectin. Plates were coated with vitronectin as previously described with small modifications. In brief, plates were coated with 0.2 µg/cm² of vitronectin (Promega) for 2 hrs at 37° C. in DPBS. Well were rinsed twice with DPBS before cell plating.

Cell Proliferation Assays.

Proliferation was assayed as described. Briefly, HUVEC cells (4×10³ per well) were placed in 96 well plates in growth factor-containing EBM-2 media for overnight h at 37° C./5% $CO_2$. Cells were incubated in growth factor and serum-free EBM-2 medium for 20 h at 37° C./5% $CO_2$ to suppress growth. Cells were then incubated with varying concentrations of engineered scmVEGF proteins and 1 nM VEGF121 for 48 h at 37° C./5% CO2. For the last 24 h of incubation, 1 µCi (20 Ci/mmol) [³H]thymidine were added to each well in 50 µl of EBM-2 media. Plates were then frozen at −80° C. and thawed again at room temperature. [³H]thymidine incorporation was be measured by harvesting the cells onto glass fiber filtermats using a Mach IIIM harvester and performing scintillation counting with a Wallac MicroBeta. Unstimulated and VEGF121-stimulated cells were used as negative and positive controls, respectively. The above assay was also done in the presence of Assay vitronectin as previously described. Wells were coated with vitronectin as previously described with small modifications. In brief, plates were coated with 0.2 µg/cm² of vitronectin (Promega) for 2 hrs at 37° C. in DPBS. Well were rinsed twice with DPBS before cell plating.

Vitronectin-Mediated Cell Adhesion Assays.

Assay for HUVEC adhesion to vitronectin was performed as described with small modifications. In brief, plates were coated with 0.2 µg/cm² of human vitronectin (Promega) for 2 hrs at 37° C. in DPBS. After two rinses with DPBS, wells were blocked with sterile 2 mg/ml BSA for 1 hr at room temperature and rinsed twice before cell plating. Adhesion assay was conducted as described before. Briefly, varying concentrations of scVEGF proteins were mixed with HUVEC cells and added to vitronectin-coated 96-well plates. The plates were incubated at 37° C. with 5% CO2 for 2 hrs, then the wells were washed two times with PBS. A solution of 0.2% crystal violet in 10% ethanol was added to the wells for 10 min, then the wells were washed three times with PBS. Solubilization buffer (a 1:1 mixture of 0.1 M $NaH_2PO_4$ and ethanol) was added and the plate was gently rocked for 15 min to completely solubilize the crystal violet. Absorbance of the wells was measured at 600 nm with a microtiter plate reader (BioTek Instruments), and data were background subtracted with a negative control containing no cells. $IC_{50}$ values were generated by fitting a sigmoidal curve to plots of log concentration peptide versus percent adhesion. Data was normalized using samples containing no competing protein. Data are presented as average values with standard deviations. Experiments were performed at least three times.

TABLE 6

Libraries used for testing VEGF loop tolerance.

Loop 1A: ΔNDAGLE (Replace with loop sizes 6, 7, 8, 9)
Loop 1B: ΔNDAGL (Replace with loop sizes 6, 7, 8, 9)
Loop 2A: ΔYPDEIEYA (Replace with loop sizes 7, 8, 9)
Loop 2B: ΔYPDEIEY (Replace with loop sizes 7, 8, 9)
Loop 2C: ΔPDEIEYA (Replace with loop sizes 7, 8, 9)
Loop 2D: ΔPDEIEY (Replace with loop sizes 7, 8, 9)
Loop 2E: ΔDEIEYA (Replace with loop sizes 7, 8, 9)
Loop 2F: ΔDEIEY (Replace with loop sizes 7, 8, 9)
Loop 3A: ΔIKPHQGQ (Replace with loop sizes 7, 8, 9)
Loop 3B: ΔIKPHQG (Replace with loop sizes 7, 8, 9)

Sequences

SEQ ID NO:1 shows the amino acid sequence of VEGF-121. SEQ ID NO:2 shows the 97-amino acid core region of VEGF-121 which was used to create the single-chain VEGF variants of the present invention. SEQ ID NO:3 shows the amino acid sequence of a single-chain variant of VEGF consisting of two identical core domains joined by a linker (MW=25249.7; $\epsilon 278=13616$ $M^{-1}cm^{-1}=0.5393$ $(mg/mL)^{-1}cm^{-1}$). SEQ ID NO:4 shows the amino acid sequence of a single-chain variant of VEGF with amino acid mutations that abolish binding to VEGFR2 at one pole, but allow binding at the opposite pole (MW=25031.4, $\epsilon 278=13616$ $M^{-1}cm^{-1}=0.5440$ $(mg/mL)^{-1}cm^{-1}$). SEQ ID NO:5 is scVEGF$_{RGD}$-7B comprising an RGD motif (MW=24927.3, $\epsilon 278=12216$ $M^{-1}cm^{-1}=0.4901$ $(mg/mL)^{-1}cm^{-1}$). SEQ ID NO:6 is scVEGF$_{RGD}$-7H (MW=24883.2, $\epsilon 278=13616$ $M^{-1}cm^{-1}=0.5472$ $(mg/mL)^{-1}cm^{-1}$). SEQ ID NO:7 is scVEGF$_{RGD}$-7I (MW=25132.5, $\epsilon 278=12216$ $M^{-1}cm^{-1}=0.4861$ $(mg/mL)^{-1}cm^{-1}$). SEQ ID NO:8 is scVEGF$_{RGD}$-7P (MW=24887.2, $\epsilon 278=12216$ $M^{-1}cm^{-1}=0.4909$ $(mg/mL)^{-1}cm^{-1}$).

SEQ ID NO:10-18 provides the amino acid sequence of scVEGFmut affinity matured sequences.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

---

What is claimed is:

1. A polypeptide comprising an integrin-recognition RGD motif having a sequence selected from the group consisting of: SEQ ID NOs: 29-35, 37-40, 42-53, 55, and 55-64.

2. A composition comprising a polypeptide according to claim 1 and a pharmaceutically acceptable excipient.

* * * * *